US011359207B2

(12) United States Patent
Gray

(10) Patent No.: US 11,359,207 B2
(45) Date of Patent: Jun. 14, 2022

(54) INCREASING PLANT GROWTH AND YIELD BY USING A GLUTAREDOXIN

(71) Applicant: BENSON HILL, INC., St. Louis, MO (US)

(72) Inventor: Benjamin Neil Gray, St. Louis, MO (US)

(73) Assignee: BENSON HILL, INC., St. Louis, MO (US)

( * ) Notice: Subject to any disclaimer, the term of this patent is extended or adjusted under 35 U.S.C. 154(b) by 113 days.

(21) Appl. No.: 16/639,375

(22) PCT Filed: Aug. 15, 2018

(86) PCT No.: PCT/IB2018/056128
§ 371 (c)(1),
(2) Date: Feb. 14, 2020

(87) PCT Pub. No.: WO2019/035003
PCT Pub. Date: Feb. 21, 2019

(65) Prior Publication Data
US 2020/0255850 A1    Aug. 13, 2020

Related U.S. Application Data

(60) Provisional application No. 62/546,673, filed on Aug. 17, 2017.

(51) Int. Cl.
*C12N 15/82* (2006.01)
*C12N 9/02* (2006.01)

(52) U.S. Cl.
CPC ....... *C12N 15/8261* (2013.01); *C12N 9/0004* (2013.01); *C12Y 120/04001* (2013.01)

(58) Field of Classification Search
None
See application file for complete search history.

(56) References Cited

U.S. PATENT DOCUMENTS 8,455,718 B2 * 6/2013 Dasgupta ........... C12N 15/8241
800/287
2006/0107345 A1 5/2006 Alexandrov et al.

FOREIGN PATENT DOCUMENTS

WO    WO 2004/018687 A2    3/2004
WO    WO 2010/039750 A2    4/2010

OTHER PUBLICATIONS

El-Kereamy et al, Frontiers in Plant Science, vol. 6: 1-12, Nov. 3, 2015 (Year: 2015).*
Hu et al, Horticulture Research 2: 1-11, 2015 (Year: 2015).*
Sequence Accession AYJ40304, Nov. 25, 2010, sequence alignnment attached to the office action. (Year: 2010).*
Sequence Accession Z99767, Nov. 14, 2006, sequence alignment attached to the office action. (Year: 2006).*

* cited by examiner

*Primary Examiner* — Elizabeth F McElwain
(74) *Attorney, Agent, or Firm* — Womble Bond Dickinson (US) LLP

(57) ABSTRACT

Compositions and methods for improving plant growth are provided herein. Polynucleotides encoding glutaredoxin proteins, polypeptides encompassing glutaredoxin proteins, and expression constructs for expressing genes of interest whose expression may improve agronomic properties including but not limited to crop yield, biotic and abiotic stress tolerance, and early vigor, plants comprising the polynucleotides, polypeptides, and expression constructs, and methods of producing transgenic plants are also provided.

12 Claims, No Drawings
Specification includes a Sequence Listing.

SEQUENCE LISTING

```
<160> NUMBER OF SEQ ID NOS: 102

<210> SEQ ID NO 1
<211> LENGTH: 396
<212> TYPE: DNA
<213> ORGANISM: Zea mays
<220> FEATURE:
<221> NAME/KEY: misc_feature
<222> LOCATION: (1)..(396)
<223> OTHER INFORMATION: glutaredoxin

<400> SEQUENCE: 1
atgggcatca ccagctccac ctccagcccg acaagcagcc cggagagcag ggccatggcg      60
ctggccaagg cgaaggagat tgtcgcgagc gcgccactcg tcgtgttctc caagaccagc     120
tgcccattct gcgtcagggt gaaacagctc ttcgaaaagc tcggcgcgtc ctataaagcg     180
atcgagctcg ataaggagtc cgatggcgcc gagctccaaa acgccctgaa agagtggaca     240
gggcagcgca cagtcccaaa cgtctttatt aacgggaagc acattggggg gtgtgacgat     300
accatggccc tgaataacga tgggaaactg gtgccactgc tgacagaagc gggggccatc     360
gcgggctccg ccagcaagac cacaattacc gcgtga                              396
```

<210> SEQ ID NO 2
<211> LENGTH: 396
<212> TYPE: DNA
<213> ORGANISM: Zea mays
<220> FEATURE:
<221> NAME/KEY: misc_feature
<222> LOCATION: (1)..(396)
<223> OTHER INFORMATION: glutaredoxin

<400> SEQUENCE: 2

```
atgggcatta cttctagtac ttcaagcccg acatcttctc cagagagcag agcaatggcc      60
ctcgctaagg ccaaagaaat tgtggcctca gctcctttag tcgttttctc aaagacttct     120 tgtcctttt gtgtgagggt taaacaactt ttcgaaaaac ttggtgcttc ctataaggca      180
atcgaattgg acaaagagtc agatggggca gaattacaga atgctttgaa ggaatggaca     240
ggacaaagga cagtgcctaa tgtctttatt aacggaaaac acataggtgg atgcgatgat     300
accatggcac ttaataacga tggtaaactt gtaccgttgc ttaccgaagc aggtgcaatt     360
gcaggctctg ctagcaagac tactattacc gcatag                               396
```

<210> SEQ ID NO 3
<211> LENGTH: 131
<212> TYPE: PRT
<213> ORGANISM: Zea mays
<220> FEATURE:
<221> NAME/KEY: MISC_FEATURE
<222> LOCATION: (1)..(131)
<223> OTHER INFORMATION: glutaredoxin

<400> SEQUENCE: 3

```
Met Gly Ile Thr Ser Ser Thr Ser Ser Pro Thr Ser Ser Pro Glu Ser
1               5                   10                  15

Arg Ala Met Ala Leu Ala Lys Ala Lys Glu Ile Val Ala Ser Ala Pro
            20                  25                  30

Leu Val Val Phe Ser Lys Thr Ser Cys Pro Phe Cys Val Arg Val Lys
        35                  40                  45

Gln Leu Phe Glu Lys Leu Gly Ala Ser Tyr Lys Ala Ile Glu Leu Asp
    50                  55                  60

Lys Glu Ser Asp Gly Ala Glu Leu Gln Asn Ala Leu Lys Glu Trp Thr
65                  70                  75                  80

Gly Gln Arg Thr Val Pro Asn Val Phe Ile Asn Gly Lys His Ile Gly
                85                  90                  95

Gly Cys Asp Asp Thr Met Ala Leu Asn Asn Asp Gly Lys Leu Val Pro
            100                 105                 110

Leu Leu Thr Glu Ala Gly Ala Ile Ala Gly Ser Ala Ser Lys Thr Thr
        115                 120                 125

Ile Thr Ala
    130
```

<210> SEQ ID NO 4
<211> LENGTH: 780
<212> TYPE: DNA
<213> ORGANISM: Cauliflower Mosaic Virus
<220> FEATURE:
<221> NAME/KEY: promoter
<222> LOCATION: (1)..(780)
<223> OTHER INFORMATION: 2X35S promoter

<400> SEQUENCE: 4

```
atggtggagc acgacactct cgtctactcc aagaatatca agatacagt ctcagaagac       60 caaagggcta ttgagacttt tcaacaaagg gtaatatcgg gaaacctcct cggattccat     120
```

| | | |
|---|---|---|
| tgcccagcta tctgtcactt catcaaaagg acagtagaaa aggaaggtgg cacctacaaa | 180 |
| tgccatcatt gcgataaagg aaaggctatc gttcaagatg cctctgccga cagtggtccc | 240 |
| aaagatggac ccccacccac gaggagcatc gtggaaaaag aagacgttcc aaccacgtct | 300 |
| tcaaagcaag tggattgatg tgaacatggt ggagcacgac actctcgtct actccaagaa | 360 |
| tatcaaagat acagtctcag aagaccaaag gctattgag acttttcaac aaagggtaat | 420 |
| atcgggaaac ctcctcggat tccattgccc agctatctgt cacttcatca aaaggacagt | 480 |
| agaaaaggaa ggtggcacct acaaatgcca tcattgcgat aaaggaaagg ctatcgttca | 540 |
| agatgcctct gccgacagtg gtcccaaaga tggacccca cccacgagga gcatcgtgga | 600 |
| aaagaagac gttccaacca cgtcttcaaa gcaagtggat tgatgtgata tctccactga | 660 |
| cgtaagggat gacgcacaat cccactatcc ttcgcaagac ccttcctcta tataaggaag | 720 |
| ttcatttcat ttggagagga cacgctgaaa tcaccagtct ctctctacaa atctatctct | 780 |

<210> SEQ ID NO 5
<211> LENGTH: 209
<212> TYPE: DNA
<213> ORGANISM: Cauliflower Mosaic Virus
<220> FEATURE:
<221> NAME/KEY: terminator
<222> LOCATION: (1)..(209)
<223> OTHER INFORMATION: 35S polyA terminator

<400> SEQUENCE: 5

| | | |
|---|---|---|
| gatctgtcga tcgacaagct cgagtttctc cataataatg tgtgagtagt tcccagataa | 60 |
| gggaattagg gttcctatag ggtttcgctc atgtgttgag catataagaa acccttagta | 120 |
| tgtatttgta tttgtaaaat acttctatca ataaaatttc taattcctaa aaccaaaatc | 180 |
| cagtactaaa atccagatcc cccgaatta | 209 |

<210> SEQ ID NO 6
<211> LENGTH: 974
<212> TYPE: DNA
<213> ORGANISM: Zea mays
<220> FEATURE:
<221> NAME/KEY: promoter
<222> LOCATION: (1)..(974)
<223> OTHER INFORMATION: ZmRbcS promoter and 5'UTR

<400> SEQUENCE: 6

| | | |
|---|---|---|
| gagctccctt taatctggcg ctagatctgc atccgcggct tgcaaagata aatggcacat | 60 |
| ttagtgtgtt attttgcaat acctttcata gtagatatcc ttaaatgcag ttttaggcat | 120 |
| gtttgggtaa ttaaataaca ttttaggag gagttttaga tttaccttttc tttcgtgatg | 180 |
| actgatgaca gacgtgggga attcaaatgc aactctagcg aaagttcata tattttcat | 240 |
| aaatagctga ggctggggta attattttt ttgtagaaaa atagaatagg tggaatggtt | 300 |
| ggggaaggcg taggcgctcg tggacgacgc ccgataaaag acaagaggcg gaattgccat | 360 |
| gaattcgagg tagctaagta aggcgcatat atatgccaaa aaattctact gtcactttcc | 420 |
| aatttcaatg cgctgccaaa caagccatcc tggaaactga cttgaattca gcccaattct | 480 |
| gtagatccaa acagggccgg cgtcagtgcc tcaggtgaga gagcagcaga cgatgcaaag | 540 |
| agccaaaact gcaagcagac gcagccgaag ccgaagccga agcccaagcc caaaactgtt | 600 |
| ttgtctttgc ccagaaccgc gacgagccta aactgcgctt cctcctatct acaagtccct | 660 |
| ggcacatcac gcatagtcca accatggcgc gcaggcgata aggcgcgcca cggggacgcg | 720 |

```
acatgtggtg gcggacgcga tcaggatagg gccaggctgg ccgggcgcgg ccacgggaga    780
acggtggcca ctcgtcccac atccgcttcg tcctgtcctg tactgcgtcc tgccccaac    840 gagagccgga gccggccatc ccgtcgcaca ctctccccct ctatatatgc cgtcggtgtg    900
ggggagccta ctacaggacg acccaagcaa gcaagcaagc agcgagtaca tacatactag    960
gcagccaggc agcc                                                      974

<210> SEQ ID NO 7
<211> LENGTH: 439
<212> TYPE: DNA
<213> ORGANISM: Zea mays
<220> FEATURE:
<221> NAME/KEY: 3'UTR
<222> LOCATION: (1)..(439)
<223> OTHER INFORMATION: ZmRbcS 3'UTR

<400> SEQUENCE: 7
accgcgcccg ccggccgccc cccgccggct agctagctag ctagctcctg cgtgagctag     60
tagctagtgc catgcgtcgt ctctgtcgtt cggttttgct tcgggtcacc gtgtacccct    120
tgcttgcttg gtttcttctt tccttttttc ctttttttt cttctttcc ccggccatgg     180 ttcctttgct ttccagcagt tctctgctgg atgtgatgta tccattgttg caatcatggc    240
cttgcattgg ctacctctat acctgctaca aaactactgc aacgcctata tatacttggg    300
gtgaggaaca tgtgaatgca agctccggct atcatataca tgtaatatgg atacaaacta    360
tatatataaa tccgccgagg cgccgacaat actatacgac accgtgttaa gttaatatat    420
aactggtgct tttattta                                                 439

<210> SEQ ID NO 8
<211> LENGTH: 741
<212> TYPE: DNA
<213> ORGANISM: Sorghum bicolor
<220> FEATURE:
<221> NAME/KEY: promoter
<222> LOCATION: (1)..(741)
<223> OTHER INFORMATION: 4XRGCGR promoter

<400> SEQUENCE: 8
gaagcgagtg gcgcgctggc ggatgaggcg gcgagtggcc cggatgcacc ggcgcaggcg     60
agcgaagcga gtggcgcgct ggcggatgag gcggcgagtg gcccggatgc accggcgcag    120
gcgagcgaag cgagtggcgc gctggcggat gaggcggcga gtggcccgga tgcaccggcg    180
caggcgagcg aagcgagtgg cgcgctggcg atgaggcgg cgagtggccc ggatgcaccg    240
gcgcaggcga gccgcacgcc gccccgcc gcggcgctcg cgcgcgcacc gctgccgcct    300
gccgccacac aatgcgagcg cgcgcgcaca cacacacaca ccaccccggc ggggggggctg    360 tagtagtaac ggccttgtct tgtcggcacg cgcgcgtccg tgtgtataag gaggcaggcc    420
cgcgacaacg ataagcggca ctcgcacgat caatgtacac attgcccgtc gcgccacca    480 catccagcat cgtcgccagc ctcgccaccc ccgcgccgtc ctcctcctcc ggctccggct    540
ccggccgccc caggcccagg ctcatccgga acgcccccgt cttcgccgcc cccgccaccg    600
tcgtgtaaac gggacggcgg gcagctgagg agtcaaacga gagagatcga gagaaagaaa    660
gggagggcat ccaccagccg ccggcgataa gaggggagga gagagaggcc agagaagagg    720
aggagaagaa gaagaaatcg a                                              741

<210> SEQ ID NO 9
<211> LENGTH: 287
```

```
<212> TYPE: DNA
<213> ORGANISM: Zea mays
<220> FEATURE:
<221> NAME/KEY: 3'UTR
<222> LOCATION: (1)..(287)
<223> OTHER INFORMATION: ZmCA1 3'UTR

<400> SEQUENCE: 9
gttcaaaact agggctacgg caattctacc ggcccgccga ctcctgcatc atcataaata    60
tatatactat actatactac tacgtaccta ccgatatgca cccgagcaat gtgaatgcgt   120
cgagtactat atatctgttt tctgcatcta catatatata ccggatcaat cgcccaatgt   180
gaatgtaata agcaatatca tttttctacca cttttcattc ctaacgctga gcttttatg   240
tactatatct tatatgatga ataataatat gaccgccttg tgatcta                287

<210> SEQ ID NO 10
<211> LENGTH: 1571
<212> TYPE: DNA
<213> ORGANISM: Flaveria bidentis
<220> FEATURE:
<221> NAME/KEY: promoter
<222> LOCATION: (1)..(1571)
<223> OTHER INFORMATION: GLDC promoter and 5'UTR

<400> SEQUENCE: 10
aagctttact cctctcaact ttcaaatcat aacataaaag ttcgtaggtt tgtgttcttc    60
ccaaaaaaaa agtgattttt tttcatcggt taattcatga ttaacatttc gacattcatt   120
ccactatttc acatcatgtt ttgatgggag attgaaatag cgataaggcg aatgtgaaag   180
tgtgaaacag gatgagccac accatcacca catcacaatt tacccaaata atatcccaaa   240
gattcatacg cattttgatc cactgaaacc ccatccaatt ctatccaatg cccaccacat   300
gttcgacgat ttgcctcagt gaatcaagac caacacatgc cactgctttc tgcttttag   360
tccctgataa caaacgattg gctttcattg ctcactgtag aaagtggaga cacccaacaa   420
ctatcatctc cacgtggttc cgtgccgcct ttttgccttt catactgctg gtgcgtcatt   480
tgtcgtcatc aaagcactca cccactatca ttgatctcga aatcttgaat ctttaggttt   540
ttatgctttg atacttgaac tctacacaca gtctcgtatc tgacttttg ttatctgtgt    600
tttgctttac taaagatctc acctttaatc aagttttgaa cttttgatgg atttgtcatg   660
ataatgaaga acacatagtt attattgatt atattttgac gaatcttttt tcatgatcgt   720
taaacataat ttgagttctt tttaccttgt ctttctttga ggtttaactg tacatgaaga   780
ctgtattttg agtttattgc ataaatggtc tatatagttt gggttaaaac aactggtttt   840
aatatcaagt ttgatactag acaaaccaac ttttttgatta acttttaaaa aaattaataa   900
gtctatttgg aaaaaaattg aaaatttgat tttaaagggt taaagttct ttttgaaaag    960
ttaataagag taacttttga aatgtaactt ttaaaaaaat actgttgata aaaaaagaaa  1020
tcctaatcat gggcttagta ttgtaagtag cttggatatt gaagctaatt tttcacttta  1080
tatttataga aaagttaatg gaagtaagag gtttggatac tttttttctt aatttagacg  1140
aatgttacac atgaaaaata agcgttgttt tgtaagattt ttttaattcg caagcactaa  1200
actcctaatc aactttggg gttaaggagt aggcagtaaa ccaaaagcgt ttttgcacga   1260
tacgatgttc aaacatttga tctataacga taagtccaag tgcgttacaa aatgaaactt  1320
tggtatccaa tatgaaactg ggtgtgtagt tcagtaccaa aagcataact ttcagcctcc  1380
ttagtgactt atgactaggc aagagaacat gtgagcccaa tgtactaact ttttacccct  1440
```

```
tttattacca ccaccccagc cccccaccat gaaccgatca gaaaaagaag caagaaaaac      1500
agagcattct tgctccttct tcttcatcaa ttcaataaca ttcttcatac cattagaccc      1560
catcttacac t                                                           1571
```

```
<210> SEQ ID NO 11
<211> LENGTH: 1497
<212> TYPE: DNA
<213> ORGANISM: Oryza sativa
<220> FEATURE:
<221> NAME/KEY: promoter
<222> LOCATION: (1)..(1497)
<223> OTHER INFORMATION: OsRbcS promoter and 5'UTR

<400> SEQUENCE: 11
gaaccatacg gaattgacgg accaattgtg catacggact tagctaaaat aattgttgat        60
ttttggcaat aagaaaagcg agtagcacat aaaatctaaa gtggatgagt aaagggacaa       120
aattttatac atgttcaggc cttctcgatg agaagtaata ctatactcct gttttgggga       180
ttatatttgt cagatgttgt atcaatctga cgatcgagtt atggttattg ttggcggctg       240
ttaaatatcg attttatgcc atcaatacct gtataattta tacagaaata ataaaacatt       300
caacatagtg gtaggcttta attctaacat attccataag tgttggtgta tatttggatg       360
caggtaataa accaccgaat taggaggaaa tctagactaa gttgaaggaa attttcatcc       420
atacaagtgt tgggcttttt aactccattt taacaccaaa atgcaagccc aaaaacctgc       480
gaaatggata aggcagactg agaaggaggc ccaggccaaa acttgggcca gttgggccaa       540
gccaggtttc ggccaaatcc tgatcatcgc tgttgatctc agggtttggc atggacgctc       600
ttgatttact cctgatggca gttgcagggc atttccgatc attcgcatgc tctacaacca       660
tcatacctac ttatttaagg agctctcatc ctcacttcat atcacacact ccaatcttga       720
gctgaattat aagaggctct attgtatttt attgtatact agaattaggg aaagattaag       780
gtcgtagaag aaatcggagg aattccggag ttatcggtga tcctttttcta tttcttatac       840 tttgttattt gctttaatag aaatatcatt tcaagtaatt aagatttgtt tagtgagaac       900
tattattggc tagttcctaa ttagcgtatg agatcactgt tcactataat ccgttaaaat       960
atagtgattg ctttagtgag ttacaaacac tacagtagtt attgattgct taaacgtggt      1020
gtttagatag ttaatttcta gtggttgctg cgtatcccat agtacgttag aggcgggtgt      1080
agaggtggtg accgccctca agagcactta attcctcctt gtttgtgtac gtggtagagc      1140
gacatctggg aacagtgggt taccagtgcc tgaagtacca tgttaggatt aaaattgtaa      1200
cattgtttct cattagtaaa tcttctctac cctctaccca catttgcttt gtatccttgg      1260
tgaacctgaa gaggaactga acacacacgt tccatgagga agacactcag tactcaagcc      1320
ggaggcagca cactgcaact taagttttttc tatagctcct agcaagctag caatggctcc      1380
ctcggtgatg gcttcgtcgg ccacctccgt ggctcccttc caggggctca agtccactgc      1440
gggcctcccg gtgaaccgcc gctccagcag ctcgagcttt ggcaacgtca gcatcga         1497
```

```
<210> SEQ ID NO 12
<211> LENGTH: 1429
<212> TYPE: DNA
<213> ORGANISM: Oryza sativa
<220> FEATURE:
<221> NAME/KEY: 3'UTR
<222> LOCATION: (1)..(1429)
<223> OTHER INFORMATION: OsRbcS 3'UTR

<400> SEQUENCE: 12
```

```
gttcgcgctt tcgttccttc gtgcatgttc tttcttttc ttttttttt gtgtgtccgt    60 gttaagctgc acgtaattgt tctctcgcgc tccgacctgc cgttgttgca agagtactac   120
tacaactatc ggtctatcgt tcggtgacgg tgagacaggg cacgtgaatg caagatctcc   180
ggctatacac acgtactcat gtaatatgat gcctagagca tatctgaatc cgtcgacaat   240
gaaattttgg ttttgcaaaa tgctggtatt tgtttatcat cctggcacgt gatatttgcc   300
tagagcatct aaatcacttt tacgaaatgt gcgcgtcaac aaactgatac ggcccaaatg   360
ccagaaatta ccagcatata tagccatatc aacttttgat tcgtatatat gaaggttgat   420
ttagttagag aaattcggtt gtgagagaag gaggctagca agattcggt tgatcaagct    480 gtaccgccag gccaggacgt gctgtgcgcg cggctgtgcc gcttgaccgc agaaccatac   540
ggaattgacg gaccaattgt gcatacggac ttagctaaaa taattgttga ttttggcaa    600 taagaaaagc gagtagcaca taaaatctaa agtggatgag taaagggaca aaattttata   660
catgttcagg ccttctcgat gagaagtaat actatactcc tgttttgggg attatatttg   720
tcagatgttg tatcaatctg acgatcgagt tatggttatt gttggcggct gttaaatatc   780
gattttatgc catcaatacc tgtataattt atacagaaat aataaaacat tcaacatagt   840
ggtaggcttt aattctaaca tattccataa gtgttggtgt atatttggat gcaggtaata   900
aaccaccgaa ttaggaggaa atctagacta agttgaagga aattttcatc catacaagtg   960
ttgggctttt taactccatt ttaacaccaa aatgcaagcc caaaacctg cgaaatggat    1020 aaggcagact gagaaggagg cccaggccaa aacttgggcc agttgggcca agccaggttt   1080
cggccaaatc ctgatcatcg ctgttgatct cagggtttgg catggacgct cttgatttac   1140
tcctgatggc agttgcaggg catttccgat cattcgcatg ctctacaacc atcataccta   1200
cttatttaag gagctctcat cctcacttca tatcacacac tccaatcttg agctgaatta   1260
taagaggctc tattgtattt tattgtatac tagaattagg gaaagattaa ggtcgtagaa   1320
gaaatcggag gaattccgga gttatcggtg atccttttct atttcttata ctttgttatt   1380
tgctttaata gaaatatcat ttcaagtaat taagatttgt ttagtgaga                1429
```

<210> SEQ ID NO 13
<211> LENGTH: 1002
<212> TYPE: DNA
<213> ORGANISM: Arabidopsis thaliana
<220> FEATURE:
<221> NAME/KEY: promoter
<222> LOCATION: (1)..(1002)
<223> OTHER INFORMATION: AtSBPase promoter and 5'UTR

<400> SEQUENCE: 13

```
tttgctgtaa tattggtttc acttttctt tcatatcctt ttgtattgtg tattagggtt     60
tattctgtgt cttgcacgga cgtttgtgga ttttattgtt atatttgtca atgcttattt   120
aatatgtaaa attatgtaat aaactaaaat tatttatggt aaaccaaata gcttttttgt   180
gtttagtagg gattctagat ctttctcaaa gttttgaatt taaagatctc ttggttcaaa   240
tccattgtgg aaaggtttat gataaatgtt ggtaaagtta tagccgtatg agaggctatt   300
gagagctatt agccattaat caaactaatg aaaatcaatt tacaataacc aaaaactgaa   360
caaatgattt ttttttctaa gttaacaaaa actaaaatga aaatatgta acaaaatctt    420 ataatattcc ctgtcattcc ttagatatta atgaggaatc ttatgacatt ccaaaaatgt   480
atatttaata atctttataa atttaaaatt attatttaaa tcaaaaaatc aaagtggtgc   540
```

```
agcggaagcg tgatgggccc ataacccaca ggtcacagga tcgaaacctg tctttgatat    600
aatctttttt ttttggcaga tatattttat acaaaaataa acaaccaaat gtaatgttaa    660
cttctacttg catagccaca caaatataat ttggtttgta tgtcattggt gatgtaaact    720
gaaattgaag ataatagaat ctcataacca cacaaaaaat gaatgaacgc aaatcaaagc    780
ctctcaacac atctctttgc ctcggtctct ctctcgccca attgcccatc accagagctt    840
aatcatatct tcttcagtta ctgccacgtg tcactctgac cgtgaacagc ctttatctct    900
tccaagtcca cttgtgttct tgattatttt gtcttcacca ttctctctac tcaaagctct    960
tcttcttcga tcaaaaaacc tcgagcttct aacagtttaa ac                      1002
```

```
<210> SEQ ID NO 14
<211> LENGTH: 280
<212> TYPE: DNA
<213> ORGANISM: Arabidopsis thaliana
<220> FEATURE:
<221> NAME/KEY: 3'UTR
<222> LOCATION: (1)..(280)
<223> OTHER INFORMATION: AtSBPase 3'UTR

<400> SEQUENCE: 14
```

```
cggaccgaaa ctcattcaaa ataagtgaat gcatgtttat ttttccataa accggataat     60
ctacttttcc cttggtttat aagagaagca acaaaacttg tgatacaagt ttttttttaaa   120 aattattagt ttggtttggt gttaatcaaa attttaacaa ctaaaaacaa ataatgaaat    180
ctgtctgaaa ctttattatc atatgatcaa aaacaatgtt taagccggcg cgcccgagta    240
tcgaattcct gcaggcatgc aagcgatccc cgatcgttca                          280
```

```
<210> SEQ ID NO 15
<211> LENGTH: 128
<212> TYPE: PRT
<213> ORGANISM: Sorghum bicolor
<220> FEATURE:
<221> NAME/KEY: MISC_FEATURE
<222> LOCATION: (1)..(128)
<223> OTHER INFORMATION: glutaredoxin

<400> SEQUENCE: 15
```

```
Met Gly Ile Ala Ser Ser Ser Ser Asn Pro Glu Ser Arg Ala Met
1               5                   10                  15

Ala Leu Ala Lys Ala Lys Glu Ile Val Ala Ser Ala Pro Leu Val Val
            20                  25                  30

Phe Ser Lys Thr Ser Cys Pro Phe Cys Val Arg Val Lys Gln Leu Phe
        35                  40                  45

Glu Lys Leu Gly Ala Ser Tyr Lys Ala Ile Glu Leu Asp Val Glu Ser
    50                  55                  60

Asp Gly Pro Glu Leu Gln Asn Ala Leu Lys Glu Trp Thr Gly Gln Arg
65                  70                  75                  80

Thr Val Pro Asn Val Phe Ile Asn Gly Lys His Ile Gly Gly Cys Asp
                85                  90                  95

Asp Thr Met Ala Leu Asn Asn Asp Gly Lys Leu Val Pro Leu Leu Thr
            100                 105                 110

Glu Ala Gly Ala Ile Ala Gly Ser Thr Ser Lys Thr Thr Val Thr Ala
        115                 120                 125
```

```
<210> SEQ ID NO 16
<211> LENGTH: 130
<212> TYPE: PRT
<213> ORGANISM: Setaria italica
```

```
<220> FEATURE:
<221> NAME/KEY: MISC_FEATURE
<222> LOCATION: (1)..(130)
<223> OTHER INFORMATION: glutaredoxin

<400> SEQUENCE: 16

Met Gly Ile Ala Ser Ser Ser Ser Ser Pro Glu Ser Arg Ala Met
1               5                   10                  15

Ala Leu Thr Lys Ala Lys Glu Ile Val Ala Ser Ala Pro Val Val
                20                  25                  30

Phe Ser Lys Ser Tyr Cys Pro Phe Cys Val Arg Val Lys Gln Leu Phe
                35                  40                  45

Glu Lys Leu Gly Ala Thr Phe Lys Ala Ile Glu Leu Asp Val Glu Ser
    50                  55                  60

Asp Gly Ser Glu Leu Gln Asp Ala Leu Lys Glu Trp Thr Gly Gln Arg
65                  70                  75                  80

Thr Val Pro Asn Val Phe Ile Ser Gly Lys His Ile Gly Gly Cys Asp
                85                  90                  95

Asp Thr Met Ala Leu Asn Asn Asp Gly Lys Leu Val Pro Leu Leu Thr
                100                 105                 110

Glu Ala Gly Ala Ile Ala Gly Ser Thr Ser Lys Thr Thr Thr Thr
                115                 120             125

Thr Ala
    130

<210> SEQ ID NO 17
<211> LENGTH: 128
<212> TYPE: PRT
<213> ORGANISM: Brachypodium distachyon
<220> FEATURE:
<221> NAME/KEY: MISC_FEATURE
<222> LOCATION: (1)..(128)
<223> OTHER INFORMATION: glutaredoxin

<400> SEQUENCE: 17

Met Gly Ile Ala Ser Ser Ser Ser Thr Pro Glu Ser Arg Thr Met
1               5                   10                  15

Ala Leu Ala Lys Ala Lys Glu Ile Val Ala Ser Ala Pro Val Val
                20                  25                  30

Phe Ser Lys Ser Tyr Cys Pro Phe Cys Val Lys Val Lys Gln Leu Phe
                35                  40                  45

Thr Gln Leu Gly Ala Ser Phe Lys Ala Ile Glu Leu Asp Lys Glu Ser
    50                  55                  60

Asp Gly Ala Glu Met Gln Ser Ala Leu Ala Glu Trp Thr Gly Gln Arg
65                  70                  75                  80

Thr Val Pro Asn Val Phe Ile Asn Gly Lys His Ile Gly Gly Cys Asp
                85                  90                  95

Asp Thr Val Ala Leu Asn Asn Gly Gly Lys Leu Val Ala Leu Leu Thr
                100                 105                 110

Glu Ala Gly Ala Ile Ala Gly Ser Ala Ser Lys Ala Thr Met Thr Ala
                115                 120                 125

<210> SEQ ID NO 18
<211> LENGTH: 127
<212> TYPE: PRT
<213> ORGANISM: Oryza sativa
<220> FEATURE:
<221> NAME/KEY: MISC_FEATURE
<222> LOCATION: (1)..(127)
<223> OTHER INFORMATION: glutaredoxin
```

```
<400> SEQUENCE: 18

Met Gly Ile Ala Ser Ser Ser Ser Thr Pro Glu Ser Arg Lys Met
1               5                   10                  15

Ala Leu Ala Lys Ala Lys Glu Thr Val Ala Ser Ala Pro Val Val Val
            20                  25                  30

Tyr Ser Lys Ser Tyr Cys Pro Phe Cys Val Arg Val Lys Lys Leu Phe
            35                  40                  45

Glu Gln Leu Gly Ala Thr Phe Lys Ala Ile Glu Leu Asp Gly Glu Ser
        50                  55                  60

Asp Gly Ser Glu Leu Gln Ser Ala Leu Ala Glu Trp Thr Gly Gln Arg
65                  70                  75                  80

Thr Val Pro Asn Val Phe Ile Asn Gly Lys His Ile Gly Gly Cys Asp
                85                  90                  95

Asp Thr Leu Ala Leu Asn Asn Glu Gly Lys Leu Val Pro Leu Leu Thr
            100                 105                 110

Glu Ala Gly Ala Ile Ala Ser Ser Ala Lys Thr Thr Ile Thr Ala
        115                 120                 125

<210> SEQ ID NO 19
<211> LENGTH: 127
<212> TYPE: PRT
<213> ORGANISM: Oryza brachyantha
<220> FEATURE:
<221> NAME/KEY: MISC_FEATURE
<222> LOCATION: (1)..(127)
<223> OTHER INFORMATION: glutaredoxin

<400> SEQUENCE: 19

Met Gly Ile Ala Ala Ser Ser Ser Thr Pro Glu Ser Arg Lys Met Ala
1               5                   10                  15

Leu Ala Lys Ala Lys Glu Ile Val Ala Ser Thr Pro Val Val Val Phe
            20                  25                  30

Ser Lys Thr Tyr Cys Pro Phe Cys Val Arg Val Lys Lys Leu Phe Glu
        35                  40                  45

Gln Leu Gly Ala Thr Phe Lys Ala Ile Glu Leu Asp Val Glu Ser Asp
    50                  55                  60

Gly Pro Glu Leu Gln Ser Ala Leu Ala Glu Trp Thr Gly Gln Arg Thr
65                  70                  75                  80

Val Pro Asn Val Phe Ile Asn Gly Lys His Ile Gly Gly Cys Asp Asp
                85                  90                  95

Thr Met Ala Leu Asn Ser Ala Gly Lys Leu Val Pro Leu Leu Thr Glu
            100                 105                 110

Ala Gly Ala Ile Ala Ser Ser Gly Ala Lys Ala Thr Ala Thr Ala
        115                 120                 125

<210> SEQ ID NO 20
<211> LENGTH: 129
<212> TYPE: PRT
<213> ORGANISM: Aegilops tauschii
<220> FEATURE:
<221> NAME/KEY: MISC_FEATURE
<222> LOCATION: (1)..(129)
<223> OTHER INFORMATION: glutaredoxin

<400> SEQUENCE: 20

Met Gly Thr Ala Phe Ser Ser Ser Ser Thr Pro Glu Ser Arg Ala
1               5                   10                  15

Met Ala Leu Ala Lys Ala Lys Glu Ile Val Ala Ser Ala Pro Val Val
```

```
            20                  25                  30
Val Phe Ser Lys Ser Tyr Cys Pro Phe Cys Val Gln Val Lys Lys Leu
            35                  40                  45

Phe Thr Gln Leu Gly Ala Ser Phe Lys Ala Ile Glu Leu Asp Thr Glu
 50                  55                  60

Ser Asp Gly Pro Glu Ile Gln Ser Ala Leu Ala Glu Trp Thr Gly Gln
 65                  70                  75                  80

Arg Thr Val Pro Asn Val Phe Ile Asn Gly Lys His Ile Gly Gly Cys
                 85                  90                  95

Asp Asp Thr Val Ala Leu Asn Lys Gly Lys Leu Ile Ala Leu Leu
                100                 105                 110

Thr Glu Ala Gly Ala Ile Ser Gly Ser Ser Lys Thr Thr Val Thr
                115                 120                 125

Ala

<210> SEQ ID NO 21
<211> LENGTH: 130
<212> TYPE: PRT
<213> ORGANISM: Hordeum vulgare
<220> FEATURE:
<221> NAME/KEY: MISC_FEATURE
<222> LOCATION: (1)..(130)
<223> OTHER INFORMATION: glutaredoxin

<400> SEQUENCE: 21

Met Gly Thr Ala Phe Ser Ser Ser Ser Ser Thr Pro Glu Ser Arg
 1               5                  10                  15

Ala Met Ala Leu Ala Lys Ala Lys Glu Ile Val Ala Ser Ala Pro Val
                 20                  25                  30

Val Val Phe Ser Lys Ser Tyr Cys Pro Phe Cys Val Gln Val Lys Lys
                 35                  40                  45

Leu Phe Thr Gln Leu Gly Ala Ser Phe Lys Ala Ile Glu Leu Asp Thr
 50                  55                  60

Glu Ser Asp Gly Pro Glu Met Gln Ser Ala Leu Ala Glu Trp Thr Gly
 65                  70                  75                  80

Gln Arg Thr Val Pro Asn Val Phe Ile Asn Gly Lys His Ile Gly Gly
                 85                  90                  95

Cys Asp Asp Thr Leu Ala Leu Asn Lys Gly Gly Lys Leu Val Ala Leu
                100                 105                 110

Leu Thr Glu Ala Gly Ala Ile Ser Gly Ser Thr Ser Lys Ala Thr Thr
                115                 120                 125

Ala Ala
    130

<210> SEQ ID NO 22
<211> LENGTH: 131
<212> TYPE: PRT
<213> ORGANISM: Secale cereale x Triticum turgidum
<220> FEATURE:
<221> NAME/KEY: MISC_FEATURE
<222> LOCATION: (1)..(131)
<223> OTHER INFORMATION: glutaredoxin

<400> SEQUENCE: 22

Met Gly Thr Ala Phe Ser Ser Ser Ser Ala Ser Thr Pro Glu Ser
 1               5                  10                  15

Arg Ala Met Ala Leu Ala Lys Ala Lys Glu Ile Val Ala Ser Ala Pro
                 20                  25                  30
```

```
Val Val Val Phe Ser Lys Ser Tyr Cys Pro Phe Cys Val Gln Val Lys
         35                  40                  45

Lys Leu Leu Thr Arg Leu Gly Ala Ser Phe Lys Ala Ile Glu Leu Asp
 50                  55                  60

Thr Glu Ser Asp Gly Pro Glu Ile Gln Ser Ala Leu Ala Glu Trp Thr
 65                  70                  75                  80

Gly Gln Arg Thr Val Pro Asn Val Phe Ile Asn Gly Lys His Ile Gly
                 85                  90                  95

Gly Cys Asp Asp Thr Ile Ala Leu Asn Lys Gly Gly Lys Leu Val Ala
                100                 105                 110

Leu Leu Thr Glu Ala Gly Ala Ile Ser Gly Ser Ala Ser Glu Ala Thr
            115                 120                 125

Val Thr Ala
        130

<210> SEQ ID NO 23
<211> LENGTH: 98
<212> TYPE: PRT
<213> ORGANISM: Zea mays
<220> FEATURE:
<221> NAME/KEY: MISC_FEATURE
<222> LOCATION: (1)..(98)
<223> OTHER INFORMATION: glutaredoxin

<400> SEQUENCE: 23

Met Gly Ile Thr Ser Ser Thr Ser Ser Pro Thr Ser Ser Pro Glu Ser
 1               5                  10                  15

Arg Ala Met Ala Leu Ala Lys Ala Lys Glu Ile Val Ala Ser Ala Pro
                20                  25                  30

Leu Val Val Phe Ser Lys Thr Ser Cys Pro Phe Cys Val Arg Val Lys
             35                  40                  45

Gln Leu Phe Glu Lys Leu Gly Ala Ser Tyr Lys Ala Ile Glu Leu Asp
 50                  55                  60

Lys Glu Asn Thr Met Ala Leu Asn Asn Asp Gly Lys Leu Val Pro Leu
 65                  70                  75                  80

Leu Thr Glu Ala Gly Ala Ile Ala Gly Ser Ala Ser Lys Thr Thr Ile
                 85                  90                  95

Thr Ala

<210> SEQ ID NO 24
<211> LENGTH: 112
<212> TYPE: PRT
<213> ORGANISM: Oryza sativa
<220> FEATURE:
<221> NAME/KEY: MISC_FEATURE
<222> LOCATION: (1)..(112)
<223> OTHER INFORMATION: glutaredoxin

<400> SEQUENCE: 24

Met Ala Leu Ala Lys Ala Lys Glu Thr Val Ala Ser Ala Pro Val Val
 1               5                  10                  15

Val Tyr Ser Lys Ser Tyr Cys Pro Phe Cys Val Arg Val Lys Lys Leu
                20                  25                  30

Phe Gly Gln Leu Gly Ala Thr Phe Lys Ala Ile Glu Leu Asp Gly Glu
             35                  40                  45

Ser Asp Gly Ser Glu Leu Gln Ser Ala Leu Ala Glu Trp Thr Gly Gln
 50                  55                  60

Arg Thr Val Pro Asn Val Phe Ile Asn Gly Lys His Ile Gly Gly Cys
 65                  70                  75                  80
```

Asp Asp Thr Leu Ala Leu Asn Asn Glu Gly Lys Leu Val Pro Leu Leu
                85                  90                  95

Thr Glu Ala Gly Ala Ile Ala Ser Ala Lys Thr Thr Ile Thr Ala
            100                 105                 110

<210> SEQ ID NO 25
<211> LENGTH: 113
<212> TYPE: PRT
<213> ORGANISM: Aegilops tauschii
<220> FEATURE:
<221> NAME/KEY: MISC_FEATURE
<222> LOCATION: (1)..(113)
<223> OTHER INFORMATION: glutaredoxin

<400> SEQUENCE: 25

Met Ala Leu Ala Lys Ala Lys Glu Ile Val Ala Ser Ala Pro Val Val
1               5                   10                  15

Val Phe Ser Lys Ser Tyr Cys Pro Phe Cys Val Gln Val Lys Lys Leu
                20                  25                  30

Phe Thr Gln Leu Gly Ala Ser Phe Lys Ala Ile Glu Leu Asp Thr Glu
            35                  40                  45

Ser Asp Gly Pro Glu Ile Gln Ser Ala Leu Ala Glu Trp Thr Gly Gln
        50                  55                  60

Arg Thr Val Pro Asn Val Phe Ile Asn Gly Lys His Ile Gly Gly Cys
65                  70                  75                  80

Asp Asp Thr Val Ala Leu Asn Lys Gly Gly Lys Leu Ile Ala Leu Leu
                85                  90                  95

Thr Glu Ala Gly Ala Ile Ser Gly Ser Ser Lys Thr Thr Val Thr
            100                 105                 110

Ala

<210> SEQ ID NO 26
<211> LENGTH: 113
<212> TYPE: PRT
<213> ORGANISM: Triticum aestivum
<220> FEATURE:
<221> NAME/KEY: MISC_FEATURE
<222> LOCATION: (1)..(113)
<223> OTHER INFORMATION: glutaredoxin

<400> SEQUENCE: 26

Met Ala Leu Ala Lys Ala Lys Glu Ile Val Ala Ser Ala Pro Val Val
1               5                   10                  15

Val Phe Ser Lys Ser Tyr Cys Pro Phe Cys Val Gln Val Lys Lys Leu
                20                  25                  30

Phe Thr Gln Leu Gly Ala Ser Phe Lys Ala Ile Glu Leu Asp Thr Glu
            35                  40                  45

Ser Asp Gly Pro Glu Ile Gln Ser Ala Leu Ala Glu Trp Thr Gly Gln
        50                  55                  60

Arg Thr Val Pro Asn Val Phe Ile Asn Gly Lys His Ile Gly Gly Cys
65                  70                  75                  80

Asp Asp Thr Val Ala Leu Asn Lys Gly Gly Lys Leu Ile Ala Leu Leu
                85                  90                  95

Thr Glu Ala Gly Ala Ile Ser Gly Ser Ser Lys Thr Thr Val Thr
            100                 105                 110

Pro

<210> SEQ ID NO 27

```
<211> LENGTH: 113
<212> TYPE: PRT
<213> ORGANISM: Deschampsia antarctica
<220> FEATURE:
<221> NAME/KEY: MISC_FEATURE
<222> LOCATION: (1)..(113)
<223> OTHER INFORMATION: glutaredoxin

<400> SEQUENCE: 27
```

Met Ala Leu Ala Lys Ala Lys Glu Ile Ala Ala Ser Ser Pro Val Val
1               5                   10                  15

Val Phe Ser Lys Ser Tyr Cys Pro Tyr Cys Thr Arg Val Lys Gln Leu
            20                  25                  30

Phe Thr Lys Leu Gly Ala Ser Phe Lys Ala Ile Glu Leu Asp Val Glu
        35                  40                  45

Gly Asp Gly Ala Asp Met Gln Ser Ala Leu Ala Gln Trp Thr Gly Gln
50                  55                  60

Lys Thr Val Pro Asn Val Phe Ile Asn Gly Lys His Ile Gly Gly Cys
65                  70                  75                  80

Asp Asp Thr Leu Ala Leu Glu Lys Ser Gly Lys Leu Val Pro Leu Leu
                85                  90                  95

Arg Glu Ala Gly Ala Ile Ser Gly Ser Ala Ser Lys Glu Thr Met Thr
            100                 105                 110

Ala

```
<210> SEQ ID NO 28
<211> LENGTH: 129
<212> TYPE: PRT
<213> ORGANISM: Triticum urartu
<220> FEATURE:
<221> NAME/KEY: MISC_FEATURE
<222> LOCATION: (1)..(129)
<223> OTHER INFORMATION: glutaredoxin

<400> SEQUENCE: 28
```

Met Ala Leu Ala Lys Ala Lys Glu Ile Val Ala Ser Ala Pro Val Val
1               5                   10                  15

Val Phe Ser Lys Ser Tyr Cys Pro Phe Cys Val Gln Val Lys Lys Leu
            20                  25                  30

Leu Thr Gln Leu Gly Ala Ser Phe Lys Ala Ile Glu Met Asp Thr Glu
        35                  40                  45

Arg Leu Gly Arg Asn Leu Ile Gln Leu Thr His Val Ile Phe Tyr Glu
        50                  55                  60

Gly Asp Gly Thr Glu Ile Gln Ser Ala Leu Ala Glu Trp Thr Gly Gln
65                  70                  75                  80

Arg Thr Val Pro Asn Val Phe Ile Asn Gly Lys His Ile Gly Gly Cys
                85                  90                  95

Asp Asp Thr Ile Ala Leu Asn Lys Gly Gly Lys Leu Val Ala Leu Leu
            100                 105                 110

Thr Glu Ala Gly Ala Ile Ser Gly Ser Ser Ser Lys Thr Thr Val Thr
        115                 120                 125

Ala

```
<210> SEQ ID NO 29
<211> LENGTH: 105
<212> TYPE: PRT
<213> ORGANISM: Brachypodium distachyon
<220> FEATURE:
<221> NAME/KEY: MISC_FEATURE
<222> LOCATION: (1)..(105)
```

-continued

<223> OTHER INFORMATION: glutaredoxin

<400> SEQUENCE: 29

Met Leu Thr Leu Ile Leu Trp Ala Ile Cys Ser Lys Ser Tyr Cys Pro
1               5                   10                  15

Phe Cys Val Lys Val Lys Gln Leu Phe Thr Gln Leu Gly Ala Ser Phe
            20                  25                  30

Lys Ala Ile Glu Leu Asp Lys Glu Ser Asp Gly Ala Glu Met Gln Ser
        35                  40                  45

Ala Leu Ala Glu Trp Thr Gly Gln Arg Thr Val Pro Asn Val Phe Ile
    50                  55                  60

Asn Gly Lys His Ile Gly Gly Cys Asp Asp Thr Val Ala Leu Asn Asn
65                  70                  75                  80

Gly Gly Lys Leu Val Ala Leu Leu Thr Glu Ala Gly Ala Ile Ala Gly
                85                  90                  95

Ser Ala Ser Lys Ala Thr Met Thr Ala
            100                 105

<210> SEQ ID NO 30
<211> LENGTH: 115
<212> TYPE: PRT
<213> ORGANISM: Setaria italica
<220> FEATURE:
<221> NAME/KEY: MISC_FEATURE
<222> LOCATION: (1)..(115)
<223> OTHER INFORMATION: glutaredoxin

<400> SEQUENCE: 30

Met Ala Leu Glu Lys Ala Lys Glu Ile Val Ala Ser Ser Pro Val Val
1               5                   10                  15

Val Phe Ser Lys Thr Tyr Cys Pro Phe Cys Thr Arg Val Lys Gln Leu
            20                  25                  30

Leu Ala Gln Leu Gly Ala Asn Tyr Lys Ala Val Glu Leu Asp Val Glu
        35                  40                  45

Ser Asp Gly Ser Asp Leu Gln Ser Ala Leu Ala Glu Trp Thr Gly Gln
    50                  55                  60

Lys Thr Val Pro Asn Val Phe Ile Lys Gly Gln His Ile Gly Gly Cys
65                  70                  75                  80

Asp Ala Thr Val Ala Met His Asn Asp Gly Lys Leu Val Pro Leu Leu
                85                  90                  95

Ala Glu Ala Gly Ala Ile Ala Ser Ala Ser Lys Ala Thr Ala Thr
            100                 105                 110

Pro Ser Leu
        115

<210> SEQ ID NO 31
<211> LENGTH: 115
<212> TYPE: PRT
<213> ORGANISM: Sorghum bicolor
<220> FEATURE:
<221> NAME/KEY: MISC_FEATURE
<222> LOCATION: (1)..(115)
<223> OTHER INFORMATION: glutaredoxin

<400> SEQUENCE: 31

Met Ala Leu Glu Lys Ala Lys Glu Ile Val Ala Ser Ser Pro Val Val
1               5                   10                  15

Val Phe Ser Lys Thr Tyr Cys Pro Phe Cys Ala Arg Val Lys Gln Leu
            20                  25                  30

-continued

```
Leu Ala Gln Leu Gly Ala Ser Tyr Lys Ala Ile Glu Leu Asp Val Glu
         35                  40                  45

Ser Asp Gly Ala Asp Leu Gln Ser Ala Leu Ala Glu Trp Thr Gly Gln
 50                  55                  60

Lys Thr Val Pro Asn Val Phe Val Lys Gly Glu Arg Ile Gly Gly Cys
 65                  70                  75                  80

Asp Ala Thr Met Ala Met His Asp Gly Gly Lys Leu Val Pro Leu Leu
                 85                  90                  95

Thr Glu Ala Gly Ala Ile Val Thr Ala Ser Ala Thr Ala Thr Thr Thr
                100                 105                 110

Pro Ser Leu
        115
```

<210> SEQ ID NO 32
<211> LENGTH: 107
<212> TYPE: PRT
<213> ORGANISM: Gossypium raimondii
<220> FEATURE:
<221> NAME/KEY: MISC_FEATURE
<222> LOCATION: (1)..(107)
<223> OTHER INFORMATION: glutaredoxin

<400> SEQUENCE: 32

```
Met Ala Leu Gln Lys Ala Lys Asp Ile Val Ser Thr Asn Pro Val Val
 1               5                  10                  15

Val Phe Ser Lys Ser Tyr Cys Pro Phe Cys Val Asp Val Lys Gln Leu
                 20                  25                  30

Leu Gln Gln Leu Gly Ala Ser Phe Lys Ala Ile Glu Leu Asp Lys Glu
         35                  40                  45

Ser Asp Gly Ser Asp Ile Gln Ala Ala Leu Ala Glu Trp Thr Gly Gln
 50                  55                  60

Arg Thr Val Pro Asn Val Phe Ile Gly Gly Lys His Ile Gly Gly Cys
 65                  70                  75                  80

Asp Ser Thr Met Ala Leu His Lys Glu Gly Lys Leu Val Pro Leu Leu
                 85                  90                  95

Thr Glu Ala Gly Ala Ile Thr Lys Ser Ser Val
                100                 105
```

<210> SEQ ID NO 33
<211> LENGTH: 133
<212> TYPE: PRT
<213> ORGANISM: Oryza sativa
<220> FEATURE:
<221> NAME/KEY: MISC_FEATURE
<222> LOCATION: (1)..(133)
<223> OTHER INFORMATION: glutaredoxin

<400> SEQUENCE: 33

```
Met Gly Met Ala Gln Ser Ser Ser Ser Ser Arg Pro Ser Asp Ser
 1               5                  10                  15

Glu Gln Leu Glu Glu Pro Ser Lys Pro Val Met Ala Leu Asp Lys Ala
                 20                  25                  30

Lys Glu Ile Val Ala Ser Ser Pro Val Val Phe Ser Lys Thr Tyr
         35                  40                  45

Cys Pro Phe Cys Ala Arg Val Lys Arg Leu Leu Ala Glu Leu Ala Ala
         50                  55                  60

Ser Tyr Lys Ala Val Glu Leu Asp Val Glu Ser Asp Gly Ser Glu Leu
 65                  70                  75                  80

Gln Ser Ala Leu Ala Asp Trp Thr Gly Gln Arg Thr Val Pro Cys Val
```

```
                    85                  90                  95

Phe Ile Lys Gly Lys His Ile Gly Gly Cys Asp Asp Thr Met Ala Met
                100                 105                 110

His Lys Gly Gly Asn Leu Val Pro Leu Leu Thr Glu Ala Gly Ala Ile
            115                 120                 125

Ala Thr Pro Ser Leu
    130

<210> SEQ ID NO 34
<211> LENGTH: 107
<212> TYPE: PRT
<213> ORGANISM: Oryza sativa
<220> FEATURE:
<221> NAME/KEY: MISC_FEATURE
<222> LOCATION: (1)..(107)
<223> OTHER INFORMATION: glutaredoxin

<400> SEQUENCE: 34

Met Ala Leu Asp Lys Ala Lys Glu Ile Val Ala Ser Ser Pro Val Val
1               5                   10                  15

Val Phe Ser Lys Thr Tyr Cys Pro Phe Cys Ala Arg Val Lys Arg Leu
            20                  25                  30

Leu Ala Glu Leu Ala Ala Ser Tyr Lys Ala Val Glu Leu Asp Val Glu
        35                  40                  45

Ser Asp Gly Ser Glu Leu Gln Ser Ala Leu Ala Asp Trp Thr Gly Gln
    50                  55                  60

Arg Thr Val Pro Cys Val Phe Ile Lys Gly Lys His Ile Gly Gly Cys
65                  70                  75                  80

Asp Asp Thr Met Ala Met His Lys Gly Gly Asn Leu Val Pro Leu Leu
                85                  90                  95

Thr Glu Ala Gly Ala Ile Ala Thr Pro Ser Leu
                100                 105

<210> SEQ ID NO 35
<211> LENGTH: 107
<212> TYPE: PRT
<213> ORGANISM: Vigna radiata
<220> FEATURE:
<221> NAME/KEY: MISC_FEATURE
<222> LOCATION: (1)..(107)
<223> OTHER INFORMATION: glutaredoxin

<400> SEQUENCE: 35

Met Ala Leu Ala Lys Ala Lys Glu Ile Val Ser Ser Asn Pro Val Val
1               5                   10                  15

Val Phe Ser Lys Thr Tyr Cys Ser Phe Cys Val Arg Val Lys Gln Leu
            20                  25                  30

Phe Ala Asn Leu Gly Val Thr Tyr Lys Leu Leu Glu Leu Asp Val Glu
        35                  40                  45

Pro Asp Gly Ala Asp Ile Gln Ala Ala Leu Leu Glu Trp Thr Gly Gln
    50                  55                  60

Arg Thr Val Pro Asn Val Phe Ile Gly Gly Lys His Ile Gly Gly Cys
65                  70                  75                  80

Asp Asp Thr Thr Ala Leu His Asn Gln Gly Lys Leu Val Pro Leu Leu
                85                  90                  95

Thr Ser Ala Gly Ala Ile Thr Lys Ser Thr Ser
                100                 105

<210> SEQ ID NO 36
```

```
<211> LENGTH: 132
<212> TYPE: PRT
<213> ORGANISM: Zea mays
<220> FEATURE:
<221> NAME/KEY: MISC_FEATURE
<222> LOCATION: (1)..(132)
<223> OTHER INFORMATION: glutaredoxin

<400> SEQUENCE: 36

Met Ala Leu Glu Lys Ala Lys Glu Ile Ile Ala Ser Ser Pro Val Asp
1               5                   10                  15

Leu Ala Leu Arg Lys Ala Lys Glu Thr Val Ala Ser His Pro Val Val
            20                  25                  30

Val Phe Ser Lys Thr Tyr Cys Pro Phe Cys Thr Arg Val Lys Gln Leu
        35                  40                  45

Leu Ala Lys Leu Gly Ala Ser Tyr Lys Ala Ile Glu Leu Asp Val Glu
    50                  55                  60

Ser Asp Gly Ala Glu Leu Gln Ser Ala Leu Ala Glu Trp Thr Gly Gln
65                  70                  75                  80

Arg Thr Val Pro Asn Val Phe Val Lys Gly Glu Arg Ile Gly Gly Cys
                85                  90                  95

Asp Ala Thr Met Ala Met His Asp Gly Gly Lys Leu Val Pro Leu Leu
            100                 105                 110

Thr Glu Ala Gly Ala Ile Val Thr Ala Arg Ala Thr Ala Thr Thr Thr
        115                 120                 125

Thr Pro Ser Leu
    130

<210> SEQ ID NO 37
<211> LENGTH: 108
<212> TYPE: PRT
<213> ORGANISM: Capsicum annuum
<220> FEATURE:
<221> NAME/KEY: MISC_FEATURE
<222> LOCATION: (1)..(108)
<223> OTHER INFORMATION: glutaredoxin

<400> SEQUENCE: 37

Met Ala Leu Ala Lys Ala Lys Glu Ile Val Ser Ala Asn Pro Val Val
1               5                   10                  15

Val Phe Ser Lys Thr Tyr Cys Pro Phe Cys Val Ser Val Lys Asp Leu
            20                  25                  30

Leu Ala Lys Leu Gly Ala Ser Phe Lys Ala Val Glu Leu Asp Ser Glu
        35                  40                  45

Lys Asp Gly Ser Glu Ile Gln Ala Ala Leu Ala Glu Trp Thr Gly Gln
    50                  55                  60

Arg Thr Val Pro Asn Val Phe Ile Val Gly Lys His Ile Gly Gly Cys
65                  70                  75                  80

Asp Ala Thr Thr Ala Leu His Arg Asp Gly Lys Leu Val Pro Leu Leu
                85                  90                  95

Thr Glu Ala Gly Ala Ile Ala Lys Ser Ser Thr Ala
            100                 105

<210> SEQ ID NO 38
<211> LENGTH: 107
<212> TYPE: PRT
<213> ORGANISM: Gossypium hirsutum
<220> FEATURE:
<221> NAME/KEY: MISC_FEATURE
<222> LOCATION: (1)..(107)
<223> OTHER INFORMATION: glutaredoxin
```

<400> SEQUENCE: 38

Met Ala Leu Gln Lys Ala Lys Asp Ile Val Ser Thr Asn Pro Val Val
1               5                   10                  15

Val Phe Ser Lys Ser Tyr Cys Pro Phe Cys Val Asp Val Lys Gln Leu
            20                  25                  30

Leu Gln Gln Leu Gly Ala Ser Phe Lys Ala Ile Glu Leu Asp Arg Glu
        35                  40                  45

Ser Asp Gly Ser Asp Ile Gln Ala Ala Leu Ala Glu Trp Thr Gly Gln
    50                  55                  60

Arg Thr Val Pro Asn Val Phe Ile Gly Gly Lys His Ile Gly Gly Cys
65                  70                  75                  80

Asp Ser Thr Met Ala Leu His Lys Glu Gly Lys Leu Val Pro Leu Leu
                85                  90                  95

Thr Glu Ala Gly Ala Ile Thr Lys Ser Ser Val
            100                 105

<210> SEQ ID NO 39
<211> LENGTH: 115
<212> TYPE: PRT
<213> ORGANISM: Tilia platyphyllos
<220> FEATURE:
<221> NAME/KEY: MISC_FEATURE
<222> LOCATION: (1)..(115)
<223> OTHER INFORMATION: glutaredoxin

<400> SEQUENCE: 39

Met Ala Leu Pro Lys Ala Lys Glu Ile Val Ser Gly Asn Pro Val Val
1               5                   10                  15

Val Phe Ser Lys Ser Tyr Cys Pro Phe Cys Val Ser Val Lys Gln Leu
            20                  25                  30

Leu Glu Gln Ile Gly Ala Ser Phe Lys Ala Ile Glu Leu Asp Asn Glu
        35                  40                  45

Ser Asp Gly Ser Glu Ile Gln Ala Ala Leu Ala Glu Trp Thr Gly Gln
    50                  55                  60

Arg Thr Val Pro Asn Val Phe Ile Gly Gly Lys His Ile Gly Gly Cys
65                  70                  75                  80

Asp Ser Thr Thr Ala Met His Lys Asn Gly Lys Leu Ile Pro Leu Leu
                85                  90                  95

Thr Glu Ala Gly Ala Val Ala Thr Ala Thr Ala Val Thr Ala Thr
            100                 105                 110

Ala Ser Ala
        115

<210> SEQ ID NO 40
<211> LENGTH: 108
<212> TYPE: PRT
<213> ORGANISM: Nicotiana sylvestris
<220> FEATURE:
<221> NAME/KEY: MISC_FEATURE
<222> LOCATION: (1)..(108)
<223> OTHER INFORMATION: glutaredoxin

<400> SEQUENCE: 40

Met Ala Leu Ala Lys Ala Lys Glu Ile Val Ser Ala Asn Pro Val Val
1               5                   10                  15

Val Phe Ser Lys Thr Tyr Cys Pro Phe Cys Val Ser Val Lys Asp Leu
            20                  25                  30

Leu Ser Lys Leu Gly Ala Ser Phe Lys Ala Val Glu Leu Asp Thr Glu

```
            35                  40                  45
Lys Asp Gly Ser Glu Ile Gln Ala Ala Leu Ala Glu Trp Thr Gly Gln
     50                  55                  60

Arg Thr Val Pro Asn Val Phe Ile Gly Gly Lys His Ile Gly Gly Cys
 65                  70                  75                  80

Asp Ala Thr Thr Ala Leu His Arg Glu Gly Lys Leu Val Pro Leu Leu
                 85                  90                  95

Thr Glu Ala Gly Ala Leu Ala Lys Ser Ser Ser Ala
            100                 105

<210> SEQ ID NO 41
<211> LENGTH: 126
<212> TYPE: PRT
<213> ORGANISM: Ananas comosus
<220> FEATURE:
<221> NAME/KEY: MISC_FEATURE
<222> LOCATION: (1)..(126)
<223> OTHER INFORMATION: glutaredoxin

<400> SEQUENCE: 41

Met Gly Gly Ser Ser Ser Ser Ser Ser Ser Ser Glu Lys Arg Val
 1               5                  10                  15

Gly Ser Glu Met Ala Leu Pro Lys Ala Lys Asp Ile Val Ala Ser Thr
             20                  25                  30

Pro Val Val Val Phe Ser Lys Thr Phe Cys Pro Tyr Cys Asn Arg Val
         35                  40                  45

Lys Gln Leu Leu Ala Gln Leu Gly Ala Asn Phe Lys Ala Ile Glu Leu
     50                  55                  60

Asp Val Glu Ser Asp Gly Ser Glu Ile Gln Ala Ala Leu Leu Glu Trp
 65                  70                  75                  80

Thr Gly Gln Arg Thr Val Pro Asn Val Phe Ile Gly Gly Lys His Ile
                 85                  90                  95

Gly Gly Cys Asp Thr Val Thr Ala Lys His Asn Glu Gly Lys Leu Val
            100                 105                 110

Pro Leu Leu Thr Glu Ala Gly Ala Leu Gly Thr Ala Ala Ala
        115                 120                 125

<210> SEQ ID NO 42
<211> LENGTH: 107
<212> TYPE: PRT
<213> ORGANISM: Vigna angularis
<220> FEATURE:
<221> NAME/KEY: MISC_FEATURE
<222> LOCATION: (1)..(107)
<223> OTHER INFORMATION: glutaredoxin

<400> SEQUENCE: 42

Met Ala Leu Ala Lys Ala Lys Glu Ile Val Ser Ser Asn Pro Val Val
 1               5                  10                  15

Val Phe Ser Lys Thr Tyr Cys Ser Phe Cys Val Arg Val Lys Gln Leu
             20                  25                  30

Phe Ala Ser Leu Gly Val Thr Tyr Lys Leu Leu Glu Leu Asp Val Glu
         35                  40                  45

Ser Asp Gly Ala Asp Ile Gln Ala Ala Leu Leu Glu Trp Thr Gly Gln
     50                  55                  60

Arg Thr Val Pro Asn Val Phe Ile Gly Gly Lys His Ile Gly Gly Cys
 65                  70                  75                  80

Asp Asn Thr Thr Asp Leu His Asn Gln Gly Lys Leu Val Pro Leu Leu
                 85                  90                  95
```

Thr Ser Ala Gly Ala Ile Thr Lys Ser Thr Ala
            100                 105

<210> SEQ ID NO 43
<211> LENGTH: 108
<212> TYPE: PRT
<213> ORGANISM: Phalaenopsis equestris
<220> FEATURE:
<221> NAME/KEY: MISC_FEATURE
<222> LOCATION: (1)..(108)
<223> OTHER INFORMATION: glutaredoxin

<400> SEQUENCE: 43

Met Ala Leu Glu Lys Ala Lys Glu Val Val Ser Ser Ala Glu Val Val
1               5                   10                  15

Val Phe Ser Lys Thr Tyr Cys Pro Phe Cys Thr Arg Val Lys Asp Leu
            20                  25                  30

Phe Ser Lys Leu Gly Ala Lys His Lys Val Val Glu Leu Asp Lys Glu
        35                  40                  45

Ser Asp Gly Ser Glu Ile Gln Ser Ala Leu Ala Ala Trp Thr Gly Gln
    50                  55                  60

Arg Thr Val Pro Asn Val Phe Ile Ser Gly Lys His Ile Gly Gly Cys
65                  70                  75                  80

Asp Asn Val Met Glu Lys His Asn Glu Gly Lys Leu Val Pro Leu Leu
                85                  90                  95

Thr Glu Ser Gly Ala Leu Ala Leu Ser Ala Ser Ser
            100                 105

<210> SEQ ID NO 44
<211> LENGTH: 108
<212> TYPE: PRT
<213> ORGANISM: Nicotiana attenuata
<220> FEATURE:
<221> NAME/KEY: MISC_FEATURE
<222> LOCATION: (1)..(108)
<223> OTHER INFORMATION: glutaredoxin

<400> SEQUENCE: 44

Met Ala Leu Ala Lys Ala Lys Glu Val Val Ser Ala Asn Pro Val Val
1               5                   10                  15

Val Phe Ser Lys Thr Tyr Cys Pro Phe Cys Val Ser Val Lys Asp Leu
            20                  25                  30

Leu Ser Lys Leu Gly Ala Ser Phe Lys Ala Val Glu Leu Asp Thr Glu
        35                  40                  45

Lys Asp Gly Ser Glu Ile Gln Ala Ala Leu Ala Glu Trp Thr Gly Gln
    50                  55                  60

Arg Thr Val Pro Asn Val Phe Ile Gly Gly Lys His Ile Gly Gly Cys
65                  70                  75                  80

Asp Ala Thr Thr Ala Leu His Arg Glu Gly Lys Leu Val Pro Leu Leu
                85                  90                  95

Thr Glu Ala Gly Ala Leu Ala Lys Ser Ser Ser Ala
            100                 105

<210> SEQ ID NO 45
<211> LENGTH: 108
<212> TYPE: PRT
<213> ORGANISM: Cephalotus follicularis
<220> FEATURE:
<221> NAME/KEY: MISC_FEATURE
<222> LOCATION: (1)..(108)
<223> OTHER INFORMATION: glutaredoxin

<400> SEQUENCE: 45

Met Ala Leu Gln Lys Ala Lys Glu Ile Val Ala Ser Asp Pro Val Val
1               5                   10                  15

Val Phe Ser Lys Thr Tyr Cys Pro Tyr Cys Val Ser Val Lys Lys Leu
            20                  25                  30

Leu Asp Gln Leu Gly Ala Thr Tyr Lys Pro Tyr Glu Leu Asp Thr Glu
        35                  40                  45

Ser Asp Gly Ser Asp Ile Gln Ser Ala Leu Lys Glu Trp Thr Gly Gln
    50                  55                  60

Lys Thr Val Pro Asn Val Phe Ile Gly Gly Lys His Ile Gly Gly Cys
65                  70                  75                  80

Asp Ala Thr Thr Glu Leu Asn Arg Ala Gly Lys Leu Val Pro Leu Leu
                85                  90                  95

Thr Glu Ala Gly Ala Ile Ala Asn Thr Ser Ser Ala
            100                 105

<210> SEQ ID NO 46
<211> LENGTH: 108
<212> TYPE: PRT
<213> ORGANISM: Nicotiana tomentosiformis
<220> FEATURE:
<221> NAME/KEY: MISC_FEATURE
<222> LOCATION: (1)..(108)
<223> OTHER INFORMATION: glutaredoxin

<400> SEQUENCE: 46

Met Ala Leu Ala Lys Ala Lys Glu Ile Val Ser Ala Asn Pro Val Val
1               5                   10                  15

Val Phe Ser Lys Thr Tyr Cys Pro Phe Cys Val Ser Val Lys Asp Leu
            20                  25                  30

Leu Ser Lys Leu Gly Ala Ser Phe Asn Ala Val Glu Leu Asp Thr Glu
        35                  40                  45

Lys Asp Gly Ser Glu Ile Gln Ala Ala Leu Ala Glu Trp Thr Gly Gln
    50                  55                  60

Arg Thr Val Pro Asn Val Phe Ile Gly Gly Lys His Ile Gly Gly Cys
65                  70                  75                  80

Asp Ala Thr Thr Ala Leu His Arg Glu Gly Lys Leu Val Pro Leu Leu
                85                  90                  95

Thr Glu Ala Gly Ala Leu Ala Lys Ser Ser Ser Ala
            100                 105

<210> SEQ ID NO 47
<211> LENGTH: 107
<212> TYPE: PRT
<213> ORGANISM: Corchorus capsularis
<220> FEATURE:
<221> NAME/KEY: MISC_FEATURE
<222> LOCATION: (1)..(107)
<223> OTHER INFORMATION: glutaredoxin

<400> SEQUENCE: 47

Met Ala Leu Pro Lys Ala Lys Glu Ile Val Ser Ala Asn Pro Val Val
1               5                   10                  15

Val Phe Ser Lys Ser Tyr Cys Pro Tyr Cys Val Ser Val Lys Gln Leu
            20                  25                  30

Leu Gln Lys Leu Asp Ala Ser Phe Lys Ala Ile Glu Leu Asp Asn Glu
        35                  40                  45

Ser Asp Gly Ser Glu Ile Gln Ser Ala Leu Ala Glu Trp Thr Gly Gln

```
                 50                  55                  60
Arg Thr Val Pro Asn Val Phe Ile Gly Gly Lys His Ile Gly Cys
 65                  70                  75                  80

Asp Thr Thr Thr Ala Leu His Gln Glu Gly Lys Leu Ile Pro Leu Leu
                     85                  90                  95

Asn Gln Ala Gly Ala Ile Ala Lys Thr Ser Ala
                100                 105
```

<210> SEQ ID NO 48
<211> LENGTH: 107
<212> TYPE: PRT
<213> ORGANISM: Pyrus x bretschneideri
<220> FEATURE:
<221> NAME/KEY: MISC_FEATURE
<222> LOCATION: (1)..(107)
<223> OTHER INFORMATION: glutaredoxin

<400> SEQUENCE: 48

```
Met Ala Leu Thr Lys Ala Gln Glu Leu Val Ser Ser Asp Ser Val Val
 1               5                  10                  15

Val Phe Ser Lys Thr Tyr Cys Pro Phe Cys Val Asn Val Lys Gln Leu
                20                  25                  30

Leu Thr Gln Leu Gly Ala Ser Tyr Lys Ala Ile Glu Leu Asp Lys Glu
                35                  40                  45

Ser Asp Gly Ala Gln Ile Gln Ser Ala Leu Gly Glu Trp Thr Gly Gln
 50                  55                  60

Arg Thr Val Pro Asn Val Phe Ile Gly Gly Asn His Ile Gly Cys
 65                  70                  75                  80

Asp Lys Thr Thr Ala Leu His Lys Glu Gly Lys Leu Val Pro Leu Leu
                     85                  90                  95

Thr Gln Ala Gly Ala Val Ala Lys Thr Ser Ala
                100                 105
```

<210> SEQ ID NO 49
<211> LENGTH: 107
<212> TYPE: PRT
<213> ORGANISM: Cucumis sativus
<220> FEATURE:
<221> NAME/KEY: MISC_FEATURE
<222> LOCATION: (1)..(107)
<223> OTHER INFORMATION: glutaredoxin

<400> SEQUENCE: 49

```
Met Ala Leu Glu Lys Ala Lys Glu Ile Val Ala Ser Asn Pro Val Ala
 1               5                  10                  15

Val Phe Ser Lys Ser Tyr Cys Pro Phe Cys Val Gln Val Lys Arg Leu
                20                  25                  30

Leu Thr Lys Leu Gly Val Ser Phe Lys Ala Ile Glu Leu Asp Thr Glu
                35                  40                  45

Ser Asp Gly Arg Glu Ile Gln Ala Ala Leu Ala Gln Phe Thr Gly Gln
 50                  55                  60

Arg Thr Val Pro Asn Val Phe Ile Gly Gly Lys His Ile Gly Gly Cys
 65                  70                  75                  80

Asp Asp Thr Met Ala Leu Asn Ser Ser Gly Arg Leu Val Pro Leu Leu
                     85                  90                  95

Ala Glu Ala Gly Ala Ile Ala Lys Val Ala Ala
                100                 105
```

<210> SEQ ID NO 50

```
<211> LENGTH: 107
<212> TYPE: PRT
<213> ORGANISM: Corchorus olitorius
<220> FEATURE:
<221> NAME/KEY: MISC_FEATURE
<222> LOCATION: (1)..(107)
<223> OTHER INFORMATION: glutaredoxin

<400> SEQUENCE: 50

Met Ala Leu Pro Lys Ala Lys Glu Ile Val Ser Ala Asn Pro Val Val
1               5                   10                  15

Val Phe Ser Lys Ser Tyr Cys Pro Tyr Cys Val Ser Val Lys Gln Leu
            20                  25                  30

Leu Gln Lys Leu Asp Ala Ser Phe Lys Ala Ile Glu Leu Asp Asn Glu
        35                  40                  45

Ser Asp Gly Ser Asp Ile Gln Ser Ala Leu Ala Glu Trp Thr Gly Gln
    50                  55                  60

Arg Thr Val Pro Asn Val Phe Ile Gly Gly Lys His Ile Gly Gly Cys
65                  70                  75                  80

Asp Thr Thr Thr Ala Leu His Gln Glu Gly Lys Leu Ile Pro Leu Leu
                85                  90                  95

Asn Gln Ala Gly Ala Ile Ala Lys Thr Ser Ala
            100                 105

<210> SEQ ID NO 51
<211> LENGTH: 107
<212> TYPE: PRT
<213> ORGANISM: Cucumis melo
<220> FEATURE:
<221> NAME/KEY: MISC_FEATURE
<222> LOCATION: (1)..(107)
<223> OTHER INFORMATION: glutaredoxin

<400> SEQUENCE: 51

Met Ala Leu Glu Lys Ala Lys Glu Ile Val Ala Ser Asn Pro Val Thr
1               5                   10                  15

Val Phe Ser Lys Ser Tyr Cys Pro Phe Cys Val Gln Val Lys Arg Leu
            20                  25                  30

Leu Thr Lys Leu Gly Val Ser Phe Lys Ala Ile Glu Leu Asp Thr Glu
        35                  40                  45

Ser Asp Gly Arg Glu Val Gln Ala Ala Leu Ala Gln Phe Thr Gly Gln
    50                  55                  60

Arg Thr Val Pro Asn Val Phe Ile Gly Gly Lys His Ile Gly Gly Cys
65                  70                  75                  80

Asp Asp Thr Met Ala Leu Asn Ser Ser Gly Arg Leu Val Pro Leu Leu
                85                  90                  95

Ala Glu Ala Gly Ala Ile Ala Lys Val Ala Ala
            100                 105

<210> SEQ ID NO 52
<211> LENGTH: 109
<212> TYPE: PRT
<213> ORGANISM: Jatropha curcas
<220> FEATURE:
<221> NAME/KEY: MISC_FEATURE
<222> LOCATION: (1)..(109)
<223> OTHER INFORMATION: glutaredoxin

<400> SEQUENCE: 52

Met Ala Leu Glu Lys Ala Lys Glu Ile Val Ser Ser Asn Ser Val Val
1               5                   10                  15
```

```
Val Phe Ser Lys Thr Thr Cys Pro Cys Thr Thr Val Lys Lys Leu
             20                  25                  30

Phe Asn Gln Leu Gly Ala Ala Phe Lys Ala Ile Glu Leu Asp Thr Glu
         35                  40                  45

Ser Asp Gly Lys Glu Ile Gln Ser Ala Leu Ala Glu Trp Thr Gly Gln
     50                  55                  60

Arg Thr Val Pro Asn Val Phe Ile Gly Gly Lys His Ile Gly Gly Cys
65                  70                  75                  80

Asp Ala Thr Thr Gly Leu His Gly Glu Gly Lys Leu Val Pro Leu Leu
                 85                  90                  95

Thr Glu Ala Gly Ala Leu Ala Ala Val Ala Lys Ala
            100                 105
```

<210> SEQ ID NO 53
<211> LENGTH: 106
<212> TYPE: PRT
<213> ORGANISM: Ipomoea nil
<220> FEATURE:
<221> NAME/KEY: MISC_FEATURE
<222> LOCATION: (1)..(106)
<223> OTHER INFORMATION: glutaredoxin

<400> SEQUENCE: 53

```
Met Ala Ser Ala Lys Ala Lys Glu Ile Val Ala Ser Asn Pro Val Val
1               5                   10                  15

Val Phe Ser Lys Ser Tyr Cys Pro Phe Cys Val Asp Val Lys Lys Leu
             20                  25                  30

Leu Thr Gln Leu Gly Ala Ser Phe Lys Ala Ile Glu Leu Asp Thr Glu
         35                  40                  45

Ser Asp Gly Ser Glu Ile Gln Ser Ala Leu Ala Glu Trp Thr Gly Gln
     50                  55                  60

Arg Thr Val Pro Asn Val Phe Ile Gly Gly Lys His Ile Gly Gly Cys
65                  70                  75                  80

Asp Lys Thr Ile Ala Val Asn Gln Glu Gly Lys Leu Val Pro Leu Leu
                 85                  90                  95

Thr Glu Ala Gly Ala Leu Lys Lys Ala Ser
            100                 105
```

<210> SEQ ID NO 54
<211> LENGTH: 111
<212> TYPE: PRT
<213> ORGANISM: Capsella rubella
<220> FEATURE:
<221> NAME/KEY: MISC_FEATURE
<222> LOCATION: (1)..(111)
<223> OTHER INFORMATION: glutaredoxin

<400> SEQUENCE: 54

```
Met Ala Met Gln Lys Ala Lys Glu Ile Val Asn Ser Asp Ser Val Val
1               5                   10                  15

Val Phe Ser Lys Thr Phe Cys Pro Tyr Cys Val Arg Val Lys Glu Leu
             20                  25                  30

Leu Gln Gln Leu Gly Ala Lys Phe Lys Ala Val Glu Leu Asp Thr Glu
         35                  40                  45

Ser Asp Gly Ser Gln Ile Gln Ser Ala Leu Ala Glu Trp Thr Gly Gln
     50                  55                  60

Arg Thr Val Pro Asn Val Phe Ile Gly Gly Asn His Ile Gly Gly Cys
65                  70                  75                  80

Asp Ala Thr Ser Asn Leu His Lys Asp Gly Lys Leu Val Pro Leu Leu
```

```
                    85                  90                  95
Thr Glu Ala Gly Ala Ile Ala Gly Lys Thr Ala Thr Thr Ser Ala
                100                 105                 110

<210> SEQ ID NO 55
<211> LENGTH: 108
<212> TYPE: PRT
<213> ORGANISM: Solanum pennellii
<220> FEATURE:
<221> NAME/KEY: MISC_FEATURE
<222> LOCATION: (1)..(108)
<223> OTHER INFORMATION: glutaredoxin

<400> SEQUENCE: 55

Met Ser Leu Ala Lys Ala Lys Glu Ile Val Ser Gly Asn Pro Val Ala
1               5                   10                  15

Val Phe Ser Lys Thr Tyr Cys Pro Phe Cys Val Ser Val Lys Asp Leu
                20                  25                  30

Leu Ser Lys Leu Gly Ala Thr Phe Lys Ala Val Glu Leu Asp Ser Glu
                35                  40                  45

Lys Asp Gly Ser Glu Ile Gln Ala Ala Leu Ala Glu Trp Thr Gly Gln
    50                  55                  60

Arg Thr Val Pro Asn Val Phe Ile Gly Gly Lys His Ile Gly Gly Cys
65                  70                  75                  80

Asp Ala Thr Thr Ala Leu His Arg Glu Gly Lys Leu Val Pro Leu Leu
                85                  90                  95

Thr Glu Ala Gly Ala Ile Ala Lys Thr Ser Thr Ala
                100                 105

<210> SEQ ID NO 56
<211> LENGTH: 107
<212> TYPE: PRT
<213> ORGANISM: Sesamum indicum
<220> FEATURE:
<221> NAME/KEY: MISC_FEATURE
<222> LOCATION: (1)..(107)
<223> OTHER INFORMATION: glutaredoxin

<400> SEQUENCE: 56

Met Ala Leu Pro Lys Ala Lys Glu Leu Val Ser Thr Asn Pro Val Val
1               5                   10                  15

Val Phe Ser Lys Thr Tyr Cys Pro Phe Cys Val Thr Val Lys Glu Leu
                20                  25                  30

Leu Thr Lys Leu Gly Ala Ser Phe Lys Ala Ile Glu Leu Asp Lys Glu
                35                  40                  45

Gly Asp Gly Thr Glu Ile Gln Ser Ala Leu Ala Glu Trp Thr Gly Gln
    50                  55                  60

Arg Thr Val Pro Asn Val Phe Ile Gly Gly Lys His Ile Gly Gly Cys
65                  70                  75                  80

Asp Ala Thr Thr Gly Leu His Ala Gln Gly Lys Leu Val Pro Leu Leu
                85                  90                  95

Thr Glu Ala Gly Val Val Ala Lys Ala Ser Ala
                100                 105

<210> SEQ ID NO 57
<211> LENGTH: 107
<212> TYPE: PRT
<213> ORGANISM: Citrus clementina
<220> FEATURE:
<221> NAME/KEY: MISC_FEATURE
<222> LOCATION: (1)..(107)
```

<223> OTHER INFORMATION: glutaredoxin

<400> SEQUENCE: 57

Met Ala Leu Pro Lys Ala Gln Glu Thr Val Ser Ser Asn Ser Val Val
1               5                   10                  15

Val Phe Ser Lys Thr Phe Cys Pro Phe Cys Val Ser Val Lys Glu Leu
            20                  25                  30

Phe Gln Gln Leu Gly Val Thr Phe Lys Ala Ile Glu Leu Asp Lys Glu
        35                  40                  45

Ser Asp Gly Ser Asp Ile Gln Ser Ala Leu Ala Glu Trp Thr Gly Gln
    50                  55                  60

Lys Thr Val Pro Asn Val Phe Ile Gly Lys His Ile Gly Gly Cys
65                  70                  75                  80

Asp Ser Thr Thr Ala Leu His Gly Glu Gly Lys Leu Val Pro Leu Leu
                85                  90                  95

Thr Glu Ala Gly Ala Val Ala Lys Thr Ala Ala
            100                 105

<210> SEQ ID NO 58
<211> LENGTH: 108
<212> TYPE: PRT
<213> ORGANISM: Dendrobium catenatum
<220> FEATURE:
<221> NAME/KEY: MISC_FEATURE
<222> LOCATION: (1)..(108)
<223> OTHER INFORMATION: glutaredoxin

<400> SEQUENCE: 58

Met Ala Leu Glu Lys Ala Lys Glu Ile Val Ser Ser Asp Gln Val Val
1               5                   10                  15

Val Phe Ser Lys Thr Tyr Cys Pro Tyr Cys Thr Lys Val Lys Asp Leu
            20                  25                  30

Phe Ser Lys Leu Gly Ala Asn His Lys Val Ile Glu Leu Asp Lys Glu
        35                  40                  45

Ser Asp Gly Ser Glu Ile Gln Ala Ala Leu Ala Gln Trp Thr Gly Gln
    50                  55                  60

Arg Thr Val Pro Asn Val Phe Ile Ser Gly Asn His Ile Gly Gly Cys
65                  70                  75                  80

Asp Asn Val Met Glu Lys His Asn Gly Gly Lys Leu Val Pro Leu Leu
                85                  90                  95

Thr Glu Ser Gly Ala Leu Ala Ala Ser Ala Ser Thr
            100                 105

<210> SEQ ID NO 59
<211> LENGTH: 107
<212> TYPE: PRT
<213> ORGANISM: Phaseolus vulgaris
<220> FEATURE:
<221> NAME/KEY: MISC_FEATURE
<222> LOCATION: (1)..(107)
<223> OTHER INFORMATION: glutaredoxin

<400> SEQUENCE: 59

Met Ala Leu Ala Lys Ala Lys Glu Ile Val Ser Ser Asn Pro Val Val
1               5                   10                  15

Val Phe Ser Lys Thr Tyr Cys Pro Phe Cys Val Gln Val Lys Gln Leu
            20                  25                  30

Phe Ala Ser Leu Gly Val Thr Phe Lys Leu Ile Glu Met Asp Val Glu
        35                  40                  45

```
Pro Asp Gly Ala Asp Ile Gln Ala Ala Leu Leu Glu Trp Thr Gly Gln
    50                  55                  60

Arg Thr Val Pro Asn Val Phe Ile Gly Gly Lys His Ile Gly Gly Cys
 65                  70                  75                  80

Asp Asn Thr Thr Asp Leu Gln Asn Gln Gly Lys Leu Val Pro Leu Leu
                 85                  90                  95

Thr Ser Ala Gly Ala Ile Thr Lys Ser Thr Ala
            100                 105
```

<210> SEQ ID NO 60
<211> LENGTH: 107
<212> TYPE: PRT
<213> ORGANISM: Pyrus x bretschneideri
<220> FEATURE:
<221> NAME/KEY: MISC_FEATURE
<222> LOCATION: (1)..(107)
<223> OTHER INFORMATION: glutaredoxin

<400> SEQUENCE: 60

```
Met Ala Leu Thr Lys Ala Gln Glu Leu Val Ser Ser Asp Ser Val Val
 1               5                  10                  15

Val Phe Ser Lys Thr Tyr Cys Pro Phe Cys Val Asn Val Lys Gln Leu
                20                  25                  30

Leu Thr Gln Leu Gly Ala Thr Tyr Lys Ala Ile Glu Leu Asp Lys Glu
             35                  40                  45

Ser Asp Gly Ala Gln Ile Gln Ser Ala Leu Gly Glu Trp Thr Gly Gln
    50                  55                  60

Arg Thr Val Pro Asn Val Phe Ile Gly Gly Asn His Ile Gly Gly Cys
 65                  70                  75                  80

Asp Lys Thr Thr Ala Leu His Lys Glu Gly Lys Leu Val Pro Leu Leu
                 85                  90                  95

Thr Gln Thr Gly Ala Val Ala Lys Thr Ser Ala
            100                 105
```

<210> SEQ ID NO 61
<211> LENGTH: 107
<212> TYPE: PRT
<213> ORGANISM: Gossypium hirsutum
<220> FEATURE:
<221> NAME/KEY: MISC_FEATURE
<222> LOCATION: (1)..(107)
<223> OTHER INFORMATION: glutaredoxin

<400> SEQUENCE: 61

```
Met Ala Leu Gln Lys Ala Lys Asp Ile Ile Ser Thr Asn Thr Val Val
 1               5                  10                  15

Val Phe Ser Lys Ser Tyr Cys Pro Phe Cys Val Asp Val Lys Gln Leu
                20                  25                  30

Leu Gln Lys Leu Gly Ala Ser Phe Lys Ala Ile Glu Leu Asp Lys Glu
             35                  40                  45

Ser Asp Gly Ala Asp Ile Gln Ala Ala Leu Ala Glu Trp Thr Gly Gln
    50                  55                  60

Arg Thr Val Pro Asn Val Phe Ile Gly Gly Asn His Ile Gly Gly Cys
 65                  70                  75                  80

Asp Ser Thr Thr Gly Leu His Asn Gln Gly Lys Leu Val Pro Leu Leu
                 85                  90                  95

Thr Glu Ala Gly Ala Phe Thr Lys Ser Ser Val
            100                 105
```

-continued

```
<210> SEQ ID NO 62
<211> LENGTH: 107
<212> TYPE: PRT
<213> ORGANISM: Citrus sinensis
<220> FEATURE:
<221> NAME/KEY: MISC_FEATURE
<222> LOCATION: (1)..(107)
<223> OTHER INFORMATION: glutaredoxin

<400> SEQUENCE: 62
```

Met Ala Leu Pro Lys Ala Gln Glu Thr Val Ser Ser Asn Ser Val Val
1               5                   10                  15

Val Phe Ser Lys Thr Leu Cys Pro Phe Cys Val Ser Val Lys Glu Leu
            20                  25                  30

Phe Gln Gln Leu Gly Val Thr Phe Lys Ala Ile Glu Leu Asp Lys Glu
        35                  40                  45

Ser Asp Gly Ser Asp Ile Gln Ser Ala Leu Ala Glu Trp Thr Gly Gln
    50                  55                  60

Lys Thr Val Pro Asn Val Phe Ile Gly Gly Lys His Ile Gly Cys
65                  70                  75                  80

Asp Ser Thr Thr Ala Leu His Arg Glu Gly Lys Leu Val Pro Leu Leu
                85                  90                  95

Thr Glu Ala Gly Ala Val Ala Lys Thr Ala Ala
            100                 105

```
<210> SEQ ID NO 63
<211> LENGTH: 124
<212> TYPE: PRT
<213> ORGANISM: Ananas comosus
<220> FEATURE:
<221> NAME/KEY: MISC_FEATURE
<222> LOCATION: (1)..(124)
<223> OTHER INFORMATION: glutaredoxin

<400> SEQUENCE: 63
```

Met Gly Gly Ser Trp Ser Ser Ser Ser Glu Lys Arg Val Gly Ser
1               5                   10                  15

Glu Met Ala Leu Pro Lys Ala Lys Asp Ile Val Ala Ser Thr Pro Val
            20                  25                  30

Val Val Phe Ser Lys Thr Phe Cys Pro Tyr Cys Asn Arg Val Lys Gln
        35                  40                  45

Leu Leu Ala Gln Leu Gly Ala Asn Phe Lys Ala Ile Glu Leu Asp Val
    50                  55                  60

Glu Ser Asp Gly Ser Glu Ile Gln Ser Ala Leu Leu Ala Trp Thr Gly
65                  70                  75                  80

Gln Arg Thr Val Pro Asn Val Phe Ile Gly Gly Lys His Ile Gly Gly
                85                  90                  95

Cys Asp Thr Val Thr Ala Lys His Asn Glu Gly Lys Leu Val Pro Leu
            100                 105                 110

Leu Thr Glu Ala Gly Ala Leu Ala Thr Ala Ala Ala
        115                 120

```
<210> SEQ ID NO 64
<211> LENGTH: 111
<212> TYPE: PRT
<213> ORGANISM: Arabidopsis thaliana
<220> FEATURE:
<221> NAME/KEY: MISC_FEATURE
<222> LOCATION: (1)..(111)
<223> OTHER INFORMATION: glutaredoxin

<400> SEQUENCE: 64
```

```
Met Ala Met Gln Lys Ala Lys Glu Ile Val Asn Ser Glu Ser Val Val
1               5                   10                  15

Val Phe Ser Lys Thr Tyr Cys Pro Tyr Cys Val Arg Val Lys Glu Leu
            20                  25                  30

Leu Gln Gln Leu Gly Ala Lys Phe Lys Ala Val Glu Leu Asp Thr Glu
        35                  40                  45

Ser Asp Gly Ser Gln Ile Gln Ser Gly Leu Ala Glu Trp Thr Gly Gln
50                  55                  60

Arg Thr Val Pro Asn Val Phe Ile Gly Gly Asn His Ile Gly Gly Cys
65              70                  75                  80

Asp Ala Thr Ser Asn Leu His Lys Asp Gly Lys Leu Val Pro Leu Leu
                85                  90                  95

Thr Glu Ala Gly Ala Ile Ala Gly Lys Thr Ala Thr Thr Ser Ala
                100                 105                 110
```

<210> SEQ ID NO 65
<211> LENGTH: 108
<212> TYPE: PRT
<213> ORGANISM: Solanum lycopersicum
<220> FEATURE:
<221> NAME/KEY: MISC_FEATURE
<222> LOCATION: (1)..(108)
<223> OTHER INFORMATION: glutaredoxin

<400> SEQUENCE: 65

```
Met Ser Leu Ala Lys Ala Lys Glu Ile Val Ser Gly Asn Pro Val Ala
1               5                   10                  15

Val Phe Ser Lys Thr Tyr Cys Pro Phe Cys Val Ser Val Lys Asp Leu
            20                  25                  30

Leu Ser Lys Leu Gly Ala Thr Phe Lys Ala Val Glu Leu Asp Ser Glu
        35                  40                  45

Lys Asp Gly Ser Glu Ile Gln Ala Ala Leu Ala Glu Trp Thr Gly Gln
50                  55                  60

Arg Thr Val Pro Asn Val Phe Ile Gly Gly Lys His Ile Gly Gly Cys
65              70                  75                  80

Asp Ala Thr Thr Ala Leu His Arg Glu Gly Lys Leu Leu Pro Leu Leu
                85                  90                  95

Thr Glu Ala Gly Ala Ile Ala Lys Thr Ser Thr Ala
                100                 105
```

<210> SEQ ID NO 66
<211> LENGTH: 108
<212> TYPE: PRT
<213> ORGANISM: Solanum tuberosum
<220> FEATURE:
<221> NAME/KEY: MISC_FEATURE
<222> LOCATION: (1)..(108)
<223> OTHER INFORMATION: glutaredoxin

<400> SEQUENCE: 66

```
Met Ser Leu Ala Lys Ala Lys Glu Ile Val Ser Gly Asn Pro Val Ala
1               5                   10                  15

Val Phe Ser Lys Thr Tyr Cys Pro Phe Cys Val Ser Val Lys Asp Leu
            20                  25                  30

Leu Ser Lys Leu Gly Ala Thr Phe Lys Ala Val Glu Leu Asp Ser Glu
        35                  40                  45

Lys Asp Gly Ser Glu Ile Gln Ala Ala Leu Ala Glu Trp Thr Gly Gln
50                  55                  60
```

-continued

Arg Thr Val Pro Asn Val Phe Ile Gly Gly Lys His Ile Gly Gly Cys
65                  70                  75                  80

Asp Ala Thr Thr Ala Leu His Arg Glu Gly Lys Leu Val Pro Leu Leu
                85                  90                  95

Thr Glu Ala Gly Ala Leu Ala Lys Thr Ser Thr Ala
            100                 105

<210> SEQ ID NO 67
<211> LENGTH: 108
<212> TYPE: PRT
<213> ORGANISM: Eutrema salsugineum
<220> FEATURE:
<221> NAME/KEY: MISC_FEATURE
<222> LOCATION: (1)..(108)
<223> OTHER INFORMATION: glutaredoxin

<400> SEQUENCE: 67

Met Ala Met Gln Lys Ala Lys Glu Ile Val Ser Ser Asn Ala Val Val
1               5                   10                  15

Val Phe Ser Lys Ser Tyr Cys Pro Phe Cys Val Lys Val Lys Glu Leu
                20                  25                  30

Leu Gln Lys Leu Gly Ala Lys Phe Ile Ala Val Glu Leu Asp Lys Glu
            35                  40                  45

Ser Asp Gly Gly Ser Ile Gln Ala Ala Leu Gly Glu Trp Thr Gly Gln
        50                  55                  60

Arg Thr Val Pro Asn Val Phe Ile Gly Gly Lys His Ile Gly Gly Cys
65                  70                  75                  80

Asp Ala Thr Met Gly Met His Ser Ser Gly Lys Leu Val Pro Leu Leu
                85                  90                  95

Thr Glu Ala Gly Ala Ile Ala Ala Thr Thr Ser Ala
            100                 105

<210> SEQ ID NO 68
<211> LENGTH: 107
<212> TYPE: PRT
<213> ORGANISM: Herrania umbratica
<220> FEATURE:
<221> NAME/KEY: MISC_FEATURE
<222> LOCATION: (1)..(107)
<223> OTHER INFORMATION: glutaredoxin

<400> SEQUENCE: 68

Met Ala Leu Pro Lys Ala Lys Glu Ile Val Ser Ala Asn Pro Val Val
1               5                   10                  15

Val Phe Ser Lys Thr Tyr Cys Pro Tyr Cys Val Asp Val Lys Lys Leu
                20                  25                  30

Leu Gln Gln Leu Gly Ala Ser Phe Lys Ala Ile Glu Leu Asn Asn Glu
            35                  40                  45

Ser Asp Gly Ser Glu Ile Gln Ala Ala Leu Ala Glu Trp Thr Gly Gln
        50                  55                  60

Arg Thr Val Pro Asn Val Phe Ile Gly Gly Lys His Ile Gly Gly Cys
65                  70                  75                  80

Asp Thr Thr Thr Ala Met His Glu Glu Gly Lys Leu Ile Pro Leu Leu
                85                  90                  95

Thr Glu Ala Gly Ala Val Ala Lys Ser Ser Gly
            100                 105

<210> SEQ ID NO 69
<211> LENGTH: 107
<212> TYPE: PRT

<213> ORGANISM: Fragaria vesca
<220> FEATURE:
<221> NAME/KEY: MISC_FEATURE
<222> LOCATION: (1)..(107)
<223> OTHER INFORMATION: glutaredoxin

<400> SEQUENCE: 69

Met Ala Leu Pro Lys Ala Lys Glu Leu Val Ser Ser Asn Thr Val Val
1               5                   10                  15

Val Phe Ser Lys Ser Tyr Cys Pro Tyr Cys Val Thr Val Lys Lys Leu
            20                  25                  30

Phe Thr Gln Leu Gly Ala Asp Phe Lys Ala Ile Glu Leu Asp Gln Glu
        35                  40                  45

Ser Asp Gly Ser Glu Leu Gln Ala Ala Leu Lys Glu Trp Thr Gly Gln
    50                  55                  60

Lys Thr Val Pro Asn Val Phe Ile Gly Gly Asn His Ile Gly Gly Cys
65                  70                  75                  80

Asp Ala Thr Gln Ala Leu His Asn Gln Gly Lys Leu Val Pro Leu Leu
                85                  90                  95

Thr Glu Ala Gly Ala Val Gly Gln Thr Thr Ala
            100                 105

<210> SEQ ID NO 70
<211> LENGTH: 107
<212> TYPE: PRT
<213> ORGANISM: (Citrus unshiu x Citrus sinensis) x Citrus reticulata
<220> FEATURE:
<221> NAME/KEY: MISC_FEATURE
<222> LOCATION: (1)..(107)
<223> OTHER INFORMATION: glutaredoxin

<400> SEQUENCE: 70

Met Ala Leu Pro Lys Ala Gln Glu Thr Val Ser Ser Asn Ser Val Val
1               5                   10                  15

Val Phe Ser Lys Thr Phe Cys Pro Phe Cys Val Ser Val Lys Glu Leu
            20                  25                  30

Phe Gln Gln Leu Gly Val Thr Phe Lys Ala Ile Glu Leu Asn Lys Glu
        35                  40                  45

Ser Asp Gly Ser Asp Ile Gln Ser Ala Leu Ala Glu Trp Thr Gly Gln
    50                  55                  60

Lys Thr Val Pro Asn Val Phe Ile Gly Gly Lys His Ile Gly Gly Cys
65                  70                  75                  80

Asp Ser Thr Thr Ala Leu His Arg Glu Gly Lys Leu Val Pro Leu Leu
                85                  90                  95

Thr Glu Ala Gly Ala Val Ala Lys Thr Ala Ala
            100                 105

<210> SEQ ID NO 71
<211> LENGTH: 106
<212> TYPE: PRT
<213> ORGANISM: Musa acuminata
<220> FEATURE:
<221> NAME/KEY: MISC_FEATURE
<222> LOCATION: (1)..(106)
<223> OTHER INFORMATION: glutaredoxin

<400> SEQUENCE: 71

Met Ala Leu Glu Lys Ala Lys Glu Thr Val Ser Ser Asn Pro Val Val
1               5                   10                  15

Val Phe Ser Lys Thr Phe Cys Pro Phe Cys Val Arg Val Lys Lys Leu
            20                  25                  30

```
Leu Asp Gln Leu Gly Ala Arg Tyr Lys Ala Ile Glu Leu Asp Val Glu
            35                  40                  45

Ser Asp Gly Ser Asp Ile Gln Ala Ala Leu Ala Glu Trp Thr Gly Gln
 50                  55                  60

Arg Thr Val Pro Asn Val Phe Ile Gly Lys His Ile Gly Gly Cys
 65                  70                  75                  80

Asp Asp Thr Leu Ala Lys His Gln Gln Gly Lys Leu Lys Pro Leu Leu
                    85                  90                  95

Ile Glu Ala Gly Ala Leu Ala Ser Ala Ala
                100                 105
```

<210> SEQ ID NO 72
<211> LENGTH: 129
<212> TYPE: PRT
<213> ORGANISM: Ananas comosus
<220> FEATURE:
<221> NAME/KEY: MISC_FEATURE
<222> LOCATION: (1)..(129)
<223> OTHER INFORMATION: glutaredoxin

<400> SEQUENCE: 72

```
Met Gly Gly Ser Trp Ser Ser Ser Ser Ser Ser Ser Ser Ser Glu Lys
 1               5                  10                  15

Arg Val Gly Ser Glu Met Ala Leu Pro Lys Ala Lys Asp Ile Val Ala
                20                  25                  30

Ser Thr Pro Val Val Phe Ser Lys Thr Tyr Cys Pro Tyr Cys Asn
            35                  40                  45

Gln Val Lys Gln Leu Leu Ala Gln Leu Gly Ala Asn Phe Lys Ala Ile
 50                  55                  60

Glu Leu Asp Val Lys Val Ser Asp Gly Ser Glu Ile Gln Ser Ala Leu
 65                  70                  75                  80

Leu Ala Trp Thr Gly Gln Arg Thr Val Pro Asn Val Phe Ile Gly Gly
                    85                  90                  95

Lys His Ile Gly Gly Cys Asp Thr Val Thr Ala Lys His Asn Glu Gly
                100                 105                 110

Lys Leu Val Pro Leu Leu Thr Glu Ala Gly Ala Leu Ala Thr Ala Ala
                115                 120                 125

Ala
```

<210> SEQ ID NO 73
<211> LENGTH: 107
<212> TYPE: PRT
<213> ORGANISM: Malus domestica
<220> FEATURE:
<221> NAME/KEY: MISC_FEATURE
<222> LOCATION: (1)..(107)
<223> OTHER INFORMATION: glutaredoxin; X=any amino acid

<400> SEQUENCE: 73

```
Met Ala Leu Thr Lys Ala Lys Glu Leu Val Ser Thr Asn Ser Val Val
 1               5                  10                  15

Val Phe Ser Lys Thr His Cys Pro Phe Cys Val Asn Val Lys Gln Leu
                20                  25                  30

Leu Thr Gln Leu Gly Ala Ser Tyr Lys Ala Ile Glu Leu Asp Ser Glu
            35                  40                  45

Ser Asp Gly Ala Gln Ile Gln Ser Ala Leu Ala Glu Trp Thr Gly Gln
 50                  55                  60

Arg Thr Val Pro Asn Val Phe Ile Xaa Gly Asn His Ile Gly Gly Cys
```

```
                65                  70                  75                  80
Asp Lys Thr Thr Ala Leu His Lys Glu Gly Lys Leu Xaa Pro Leu Leu
                    85                  90                  95

Thr Gln Ala Gly Xaa Val Ala Lys Thr Ser Thr
                100                 105
```

<210> SEQ ID NO 74
<211> LENGTH: 111
<212> TYPE: PRT
<213> ORGANISM: Arabidopsis lyrata
<220> FEATURE:
<221> NAME/KEY: MISC_FEATURE
<222> LOCATION: (1)..(111)
<223> OTHER INFORMATION: glutaredoxin

<400> SEQUENCE: 74

```
Met Ala Ser Gln Lys Ala Lys Asp Ile Val Asn Ser Asp Ser Val Val
1               5                   10                  15

Val Phe Ser Lys Thr Tyr Cys Pro Tyr Cys Val Arg Val Lys Glu Leu
            20                  25                  30

Leu Gln Gln Leu Gly Ala Lys Phe Lys Ala Val Glu Leu Asp Asn Glu
        35                  40                  45

Ser Asp Gly Ser Gln Ile Gln Ser Ala Leu Ala Glu Trp Thr Gly Gln
    50                  55                  60

Arg Thr Val Pro Asn Val Phe Ile Gly Gly Asn His Ile Gly Gly Cys
65                  70                  75                  80

Asp Ala Thr Thr Asn Leu His Lys Asp Gly Lys Leu Val Pro Leu Leu
                85                  90                  95

Thr Glu Ala Gly Ala Ile Ala Gly Lys Thr Ala Thr Ser Ala
            100                 105                 110
```

<210> SEQ ID NO 75
<211> LENGTH: 129
<212> TYPE: PRT
<213> ORGANISM: Ananas comosus
<220> FEATURE:
<221> NAME/KEY: MISC_FEATURE
<222> LOCATION: (1)..(129)
<223> OTHER INFORMATION: glutaredoxin

<400> SEQUENCE: 75

```
Met Gly Gly Ser Trp Ser Ser Ser Ser Ser Ser Ser Ser Ser Ser Glu
1               5                   10                  15

Lys Arg Val Gly Ser Glu Met Ala Leu Pro Lys Ala Lys Asp Ile Val
            20                  25                  30

Ala Ser Thr Pro Val Val Val Phe Ser Lys Thr Tyr Cys Pro Tyr Cys
        35                  40                  45

Asn Gln Val Lys Gln Leu Leu Ala Gln Leu Gly Ala Asn Phe Lys Ala
    50                  55                  60

Ile Glu Leu Asp Val Glu Ser Asp Gly Ser Glu Ile Gln Ser Ala Leu
65                  70                  75                  80

Leu Ala Trp Thr Gly Gln Arg Thr Val Pro Asn Val Phe Ile Gly Gly
                85                  90                  95

Lys His Ile Gly Gly Cys Asp Thr Val Thr Ala Lys His Asn Glu Arg
            100                 105                 110

Lys Leu Val Pro Leu Leu Thr Glu Ala Gly Ala Leu Ala Thr Ala Ala
        115                 120                 125

Ala
```

<210> SEQ ID NO 76
<211> LENGTH: 107
<212> TYPE: PRT
<213> ORGANISM: Trifolium subterraneum
<220> FEATURE:
<221> NAME/KEY: MISC_FEATURE
<222> LOCATION: (1)..(107)
<223> OTHER INFORMATION: glutaredoxin

<400> SEQUENCE: 76

Met Ala Leu Pro Lys Ala Lys Glu Ile Val Ser Ser Asn Pro Val Val
1               5                   10                  15

Val Phe Ser Lys Ser Tyr Cys Pro Phe Cys Val Gln Val Lys Asn Leu
            20                  25                  30

Phe Thr Ser Leu Gly Ala Thr Phe Lys Ala Ile Glu Leu Asp Ser Glu
        35                  40                  45

Ser Asp Gly Ser Glu Ile Gln Ala Ala Leu His Glu Trp Thr Gly Gln
    50                  55                  60

Arg Thr Val Pro Asn Val Phe Ile Gly Gly Asn His Ile Gly Gly Cys
65                  70                  75                  80

Asp Ala Thr Val Asn Leu Gln Ser Gln Gly Lys Leu Val Pro Leu Leu
                85                  90                  95

Thr Ser Ala Gly Ala Ile Ser Val Lys Thr Ala
            100                 105

<210> SEQ ID NO 77
<211> LENGTH: 107
<212> TYPE: PRT
<213> ORGANISM: Malus domestica
<220> FEATURE:
<221> NAME/KEY: MISC_FEATURE
<222> LOCATION: (1)..(107)
<223> OTHER INFORMATION: glutaredoxin

<400> SEQUENCE: 77

Met Ala Leu Thr Lys Ala Gln Glu Leu Val Ser Ser Asn Ser Val Val
1               5                   10                  15

Val Phe Ser Lys Thr Asn Cys Pro Phe Cys Val Asn Val Lys Gln Leu
            20                  25                  30

Leu Thr Gln Leu Gly Val Thr Tyr Lys Ala Ile Glu Leu Asp Lys Glu
        35                  40                  45

Ser Asp Gly Ala Gln Ile Gln Ser Ala Leu Gly Glu Trp Thr Gly Leu
    50                  55                  60

Arg Thr Val Pro Asn Val Phe Ile Gly Gly Asn His Ile Gly Gly Cys
65                  70                  75                  80

Asp Lys Thr Thr Ala Leu His Lys Glu Gly Lys Leu Val Pro Leu Leu
                85                  90                  95

Thr Gln Ala Gly Ala Val Ala Lys Thr Ser Ala
            100                 105

<210> SEQ ID NO 78
<211> LENGTH: 107
<212> TYPE: PRT
<213> ORGANISM: Medicago truncatula
<220> FEATURE:
<221> NAME/KEY: MISC_FEATURE
<222> LOCATION: (1)..(107)
<223> OTHER INFORMATION: glutaredoxin

<400> SEQUENCE: 78

Met Ala Leu Pro Lys Ala Lys Glu Ile Val Ser Ser Asn Pro Val Val

```
1               5                   10                  15
Val Phe Ser Lys Ser Tyr Cys Pro Phe Cys Val Gln Val Lys Lys Leu
                20                  25                  30

Phe Thr Asp Leu Gly Val Thr Phe Lys Ala Val Glu Leu Asp Ser Glu
                35                  40                  45

Ser Asp Gly Ser Glu Ile Gln Gly Ala Leu Ala Gln Trp Thr Gly Gln
        50                  55                  60

Arg Thr Val Pro Asn Val Phe Ile Gly Asn His Ile Gly Gly Cys
65                  70                  75                  80

Asp Ser Thr Thr Asn Leu Gln Asn Gln Gly Lys Leu Val Pro Leu Leu
                85                  90                  95

Thr Ser Ala Gly Ala Ile Ser Gly Ser Thr Ser
                100                 105
```

<210> SEQ ID NO 79
<211> LENGTH: 107
<212> TYPE: PRT
<213> ORGANISM: Erythranthe guttata
<220> FEATURE:
<221> NAME/KEY: MISC_FEATURE
<222> LOCATION: (1)..(107)
<223> OTHER INFORMATION: glutaredoxin

<400> SEQUENCE: 79

```
Met Ala Leu Pro Lys Ala Lys Glu Ile Val Ser Thr Asn Ser Val Val
1               5                   10                  15

Val Phe Ser Lys Thr Tyr Cys Pro Phe Cys Val Ser Val Lys Lys Leu
                20                  25                  30

Leu Thr Glu Leu Gly Ala Ser Phe Lys Ala Ile Glu Leu Asp Thr Glu
                35                  40                  45

Gly Asp Gly Ala Glu Leu Gln Ser Ala Leu Ala Gln Leu Thr Gly Gln
        50                  55                  60

Arg Thr Val Pro Asn Val Phe Ile Ser Gly Lys His Ile Gly Gly Cys
65                  70                  75                  80

Asp Ala Thr Thr Ala Leu His Lys Gln Gly Lys Leu Val Pro Leu Leu
                85                  90                  95

Thr Glu Ala Gly Ala Val Ala Lys Ser Ser Ala
                100                 105
```

<210> SEQ ID NO 80
<211> LENGTH: 111
<212> TYPE: PRT
<213> ORGANISM: Camelina sativa
<220> FEATURE:
<221> NAME/KEY: MISC_FEATURE
<222> LOCATION: (1)..(111)
<223> OTHER INFORMATION: glutaredoxin

<400> SEQUENCE: 80

```
Met Ala Thr Gln Lys Ala Lys Asp Ile Val Asn Ser Asp Ser Val Val
1               5                   10                  15

Val Phe Ser Lys Thr Phe Cys Pro Tyr Cys Val Arg Val Lys Glu Leu
                20                  25                  30

Leu Gln Gln Leu Gly Ala Lys Phe Lys Ala Val Glu Leu Asp Thr Glu
                35                  40                  45

Ser Asp Gly Ser Gln Ile Gln Ser Ala Leu Gly Glu Trp Thr Gly Gln
        50                  55                  60

Arg Thr Val Pro Asn Val Phe Ile Gly Gly Asn His Ile Gly Gly Cys
65                  70                  75                  80
```

```
Asp Ala Thr Ser Asn Leu His Lys Asp Gly Lys Leu Val Pro Leu Leu
                85                  90                  95

Thr Glu Ala Gly Ala Ile Ala Gly Lys Thr Ala Thr Thr Ser Ala
            100                 105                 110
```

<210> SEQ ID NO 81
<211> LENGTH: 107
<212> TYPE: PRT
<213> ORGANISM: Ziziphus jujuba
<220> FEATURE:
<221> NAME/KEY: MISC_FEATURE
<222> LOCATION: (1)..(107)
<223> OTHER INFORMATION: glutaredoxin

<400> SEQUENCE: 81

```
Met Ala Leu Pro Lys Ala Lys Glu Ile Val Ser Ser Asn Pro Val Val
1               5                   10                  15

Val Phe Ser Lys Thr Tyr Cys Pro Tyr Cys Val Thr Val Lys Gln Leu
                20                  25                  30

Phe Thr Gln Leu Gly Ala Thr Phe Lys Val Ile Glu Leu Asp Thr Glu
                35                  40                  45

Ser Asp Gly Ser Glu Ile Gln Ser Ala Leu Ala Glu Ile Thr Gly Gln
    50                  55                  60

Arg Thr Val Pro Asn Val Phe Ile Gly Gly Asn His Ile Gly Gly Cys
65                  70                  75                  80

Asp Asn Thr Lys Ala Leu His Lys Asp Gly Lys Leu Ile Thr Leu Leu
                85                  90                  95

Thr Glu Ala Gly Ala Val Ala Lys Thr Ser Ser
            100                 105
```

<210> SEQ ID NO 82
<211> LENGTH: 107
<212> TYPE: PRT
<213> ORGANISM: Gossypium arboreum
<220> FEATURE:
<221> NAME/KEY: MISC_FEATURE
<222> LOCATION: (1)..(107)
<223> OTHER INFORMATION: glutaredoxin

<400> SEQUENCE: 82

```
Met Ala Leu Gln Lys Ala Lys Asp Ile Ile Ser Thr Asn Thr Val Val
1               5                   10                  15

Val Phe Ser Lys Ser Tyr Cys Pro Phe Cys Val Asp Val Lys Gln Leu
                20                  25                  30

Leu Gln Lys Leu Gly Ala Ser Phe Lys Val Ile Glu Leu Asp Lys Glu
                35                  40                  45

Ser Asp Gly Ala Asp Ile Gln Ala Ala Leu Ala Glu Trp Thr Gly Gln
    50                  55                  60

Arg Thr Val Pro Asn Val Phe Ile Gly Gly Asn His Ile Gly Gly Cys
65                  70                  75                  80

Asp Ser Thr Thr Gly Leu His Asn Gln Gly Lys Leu Val Pro Leu Leu
                85                  90                  95

Thr Glu Ala Gly Ala Phe Thr Lys Ser Ser Val
            100                 105
```

<210> SEQ ID NO 83
<211> LENGTH: 107
<212> TYPE: PRT
<213> ORGANISM: Prunus persica
<220> FEATURE:

-continued

```
<221> NAME/KEY: MISC_FEATURE
<222> LOCATION: (1)..(107)
<223> OTHER INFORMATION: glutaredoxin

<400> SEQUENCE: 83
```

Met Ala Leu Thr Lys Ala Lys Glu Ile Val Ser Ser Asn Ser Val Val
1               5                   10                  15

Val Phe Ser Lys Thr Tyr Cys Pro Tyr Cys Val Ser Val Lys Gln Leu
            20                  25                  30

Leu Thr Gln Leu Gly Ala Lys Phe Lys Ala Ile Glu Leu Asp Thr Glu
        35                  40                  45

Ser Asp Gly Ala Gln Ile Gln Ser Ala Leu Gly Glu Trp Ser Gly Gln
    50                  55                  60

Arg Thr Val Pro Asn Val Phe Ile Gly Gly Asn His Ile Gly Gly Cys
65                  70                  75                  80

Asp Thr Thr Thr Ala Leu His Lys Glu Gly Lys Leu Val Pro Leu Leu
                85                  90                  95

Ser Glu Ala Gly Ala Val Ala Lys Thr Pro Ala
            100                 105

```
<210> SEQ ID NO 84
<211> LENGTH: 107
<212> TYPE: PRT
<213> ORGANISM: Prunus avium
<220> FEATURE:
<221> NAME/KEY: MISC_FEATURE
<222> LOCATION: (1)..(107)
<223> OTHER INFORMATION: glutaredoxin

<400> SEQUENCE: 84
```

Met Ala Leu Thr Lys Ala Lys Glu Ile Val Ser Ser Asn Ser Val Val
1               5                   10                  15

Val Phe Ser Lys Thr Tyr Cys Pro Tyr Cys Val Ser Val Lys Gln Leu
            20                  25                  30

Leu Thr Gln Leu Gly Ala Asn Phe Lys Ala Ile Glu Leu Asp Thr Glu
        35                  40                  45

Ser Asp Gly Ala Gln Ile Gln Ser Ala Leu Gly Glu Trp Ser Gly Gln
    50                  55                  60

Arg Thr Val Pro Asn Val Phe Ile Gly Gly Asn His Ile Gly Gly Cys
65                  70                  75                  80

Asp Thr Thr Thr Ala Leu His Lys Glu Gly Lys Leu Val Pro Leu Leu
                85                  90                  95

Ser Gln Ala Gly Ala Val Ala Lys Thr Ser Ala
            100                 105

```
<210> SEQ ID NO 85
<211> LENGTH: 107
<212> TYPE: PRT
<213> ORGANISM: Juglans regia
<220> FEATURE:
<221> NAME/KEY: MISC_FEATURE
<222> LOCATION: (1)..(107)
<223> OTHER INFORMATION: glutaredoxin

<400> SEQUENCE: 85
```

Met Ala Leu Pro Lys Ala Lys Asp Ile Val Ala Ser Asn Pro Val Val
1               5                   10                  15

Val Phe Ser Lys Ser Tyr Cys Pro Phe Cys Val Thr Val Lys Gln Leu
            20                  25                  30

Leu Thr Gln Leu Gly Ala Thr Phe Lys Ala Ile Glu Leu Asp Thr Glu

```
                35                  40                  45
Ser Asp Gly Lys Glu Ile Gln Thr Ala Leu Ala Glu Trp Thr Gly Gln
 50                  55                  60

Lys Thr Val Pro Asn Val Phe Ile Gly Gly Asn His Ile Gly Gly Cys
 65                  70                  75                  80

Asp Lys Thr Thr Ala Leu His Lys Glu Gly Lys Leu Ile Pro Leu Leu
                 85                  90                  95

Thr Glu Ala Gly Ala Leu Pro Lys Ser Ala Ala
                100                 105
```

<210> SEQ ID NO 86
<211> LENGTH: 105
<212> TYPE: PRT
<213> ORGANISM: Punica granatum
<220> FEATURE:
<221> NAME/KEY: MISC_FEATURE
<222> LOCATION: (1)..(105)
<223> OTHER INFORMATION: glutaredoxin

<400> SEQUENCE: 86

```
Met Ala Leu Pro Lys Ala Lys Asp Val Val Ala Asn Pro Val Val
 1               5                  10                  15

Val Phe Ser Lys Ser Tyr Cys Pro Phe Cys Val Gln Val Lys Gln Leu
                 20                  25                  30

Leu Ala Asp Leu Gly Ala Thr Phe Lys Ala Ile Glu Leu Asp Gln Glu
                 35                  40                  45

Lys Asp Gly Glu Glu Val Gln Ala Ala Leu Ala Glu Trp Thr Gly Gln
 50                  55                  60

Arg Thr Val Pro Asn Val Phe Ile Gly Gly Asn His Ile Gly Gly Cys
 65                  70                  75                  80

Asp Lys Thr Thr Ala Met Asn Gly Asp Gly Lys Leu Val Pro Leu Leu
                 85                  90                  95

Thr Gln Ala Gly Ala Val Lys Ala Ser
                100                 105
```

<210> SEQ ID NO 87
<211> LENGTH: 124
<212> TYPE: PRT
<213> ORGANISM: Ananas comosus
<220> FEATURE:
<221> NAME/KEY: MISC_FEATURE
<222> LOCATION: (1)..(124)
<223> OTHER INFORMATION: glutaredoxin

<400> SEQUENCE: 87

```
Met Gly Gly Ser Trp Ser Ser Ser Ser Glu Lys Arg Val Gly Ser
 1               5                  10                  15

Glu Met Ala Leu Pro Lys Ala Lys Asp Ile Val Ala Ser Thr Pro Val
                 20                  25                  30

Val Val Phe Ser Lys Thr Tyr Cys Pro Tyr Cys Asn Gln Val Lys Gln
                 35                  40                  45

Leu Leu Ala Gln Leu Gly Ala Asn Phe Lys Ala Ile Glu Leu Asp Val
 50                  55                  60

Glu Ser Asp Gly Ser Glu Ile Gln Ser Ala Leu Leu Ala Trp Thr Gly
 65                  70                  75                  80

Gln Arg Thr Val Pro Asn Val Phe Ile Gly Gly Lys His Ile Gly Gly
                 85                  90                  95

Cys Asp Thr Val Thr Ala Lys His Asn Glu Gly Lys Leu Val Pro Leu
                100                 105                 110
```

```
Leu Thr Glu Ala Gly Ala Leu Ala Thr Ala Ala Ala
        115                 120

<210> SEQ ID NO 88
<211> LENGTH: 125
<212> TYPE: PRT
<213> ORGANISM: Phoenix dactylifera
<220> FEATURE:
<221> NAME/KEY: MISC_FEATURE
<222> LOCATION: (1)..(125)
<223> OTHER INFORMATION: glutaredoxin

<400> SEQUENCE: 88

Met Gly Gly Leu Trp Ser Ser Arg Ser Gly Val Ser Lys Glu Glu
1               5                   10                  15

Arg Glu Met Ala Leu Ala Lys Ala Lys Glu Leu Val Ser Ser Asn Pro
            20                  25                  30

Val Met Val Phe Ser Lys Ser Tyr Cys Ser Phe Cys Thr Arg Val Lys
        35                  40                  45

Gln Leu Leu Ser Gln Leu Gly Ala Asn Tyr Lys Val Ile Glu Leu Asp
    50                  55                  60

Val Glu Ser Asp Gly Ser Glu Ile Gln Ser Ala Leu Ala Glu Trp Thr
65                  70                  75                  80

Ala Gln Arg Thr Val Pro Asn Val Phe Ile Gly Gly Asn His Ile Gly
                85                  90                  95

Gly Cys Asp Ser Val Met Gly Arg His Asn Gly Gly Lys Leu Val Pro
            100                 105                 110

Leu Leu Thr Glu Ala Gly Ala Leu Ala Gly Pro Ala Ala
        115                 120                 125

<210> SEQ ID NO 89
<211> LENGTH: 107
<212> TYPE: PRT
<213> ORGANISM: Pyrus x bretschneideri
<220> FEATURE:
<221> NAME/KEY: MISC_FEATURE
<222> LOCATION: (1)..(107)
<223> OTHER INFORMATION: glutaredoxin

<400> SEQUENCE: 89

Met Glu Leu Thr Lys Ala Lys Glu Leu Val Ser Thr Asn Ser Val Val
1               5                   10                  15

Val Phe Ser Lys Thr Tyr Cys Pro Phe Cys Val Asn Val Lys Gln Leu
            20                  25                  30

Leu Thr Gln Leu Gly Ala Ser Tyr Lys Ala Phe Glu Leu Asp Ser Glu
        35                  40                  45

Ser Asp Gly Ala Gln Ile Gln Ser Ala Leu Ala Glu Trp Thr Gly Gln
    50                  55                  60

Arg Thr Val Pro Asn Val Phe Val Gly Gly Asn His Ile Gly Gly Cys
65                  70                  75                  80

Asp Glu Thr Thr Ala Leu His Lys Glu Gly Lys Leu Val Pro Leu Leu
                85                  90                  95

Thr Gln Ala Gly Ala Val Ala Lys Thr Ser Thr
        100                 105

<210> SEQ ID NO 90
<211> LENGTH: 107
<212> TYPE: PRT
<213> ORGANISM: Macleaya cordata
<220> FEATURE:
```

<221> NAME/KEY: MISC_FEATURE
<222> LOCATION: (1)..(107)
<223> OTHER INFORMATION: glutaredoxin

<400> SEQUENCE: 90

Met Ala Met Ser Lys Ala Lys Glu Val Ser Ser Asn Pro Val Val
1               5                   10                  15

Val Phe Ser Lys Thr Tyr Cys Pro Phe Cys Asp Gln Val Lys Arg Leu
                20                  25                  30

Leu Ser Gln Leu Gly Ala Ser Phe Lys Ala Ile Glu Leu Asp Lys Glu
            35                  40                  45

Ser Asp Gly Ser Glu Ile Gln Ala Ala Leu Ala Glu Trp Thr Gly Gln
50                  55                  60

Arg Thr Val Pro Asn Val Phe Ile Gly Gly Asn His Ile Gly Gly Cys
65                  70                  75                  80

Asp Thr Thr Thr Ser Met His Lys Gly Gly Lys Leu Val Pro Leu Leu
                85                  90                  95

Thr Gln Ala Gly Ala Ile Thr Thr Ser Ser Ser
            100                 105

<210> SEQ ID NO 91
<211> LENGTH: 111
<212> TYPE: PRT
<213> ORGANISM: Camelina sativa
<220> FEATURE:
<221> NAME/KEY: MISC_FEATURE
<222> LOCATION: (1)..(111)
<223> OTHER INFORMATION: glutaredoxin

<400> SEQUENCE: 91

Met Ala Thr Gln Lys Ala Lys Asp Ile Val Asn Ser Asp Ser Val Val
1               5                   10                  15

Val Phe Ser Lys Thr Phe Cys Pro Tyr Cys Val Arg Val Lys Glu Leu
                20                  25                  30

Leu Gln Gln Leu Gly Ala Lys Phe Lys Ala Val Glu Leu Asp Thr Glu
            35                  40                  45

Asn Asp Gly Ser Gln Ile Gln Ser Ala Leu Gly Glu Trp Thr Gly Gln
50                  55                  60

Arg Thr Val Pro Asn Val Phe Ile Gly Gly Asn His Ile Gly Gly Cys
65                  70                  75                  80

Asp Ala Thr Ser Asn Leu His Lys Asp Gly Lys Leu Val Pro Leu Leu
                85                  90                  95

Thr Glu Ala Gly Ala Ile Ala Gly Lys Thr Ala Thr Thr Ser Ala
            100                 105                 110

<210> SEQ ID NO 92
<211> LENGTH: 114
<212> TYPE: PRT
<213> ORGANISM: Vitis vinifera
<220> FEATURE:
<221> NAME/KEY: MISC_FEATURE
<222> LOCATION: (1)..(114)
<223> OTHER INFORMATION: glutaredoxin

<400> SEQUENCE: 92

Met Ala Leu Gln Lys Ala Gln Glu Met Val Ser Ser Asn Pro Val Val
1               5                   10                  15

Val Phe Ser Lys Thr Tyr Cys Pro Phe Cys Val Ser Val Lys Lys Leu
                20                  25                  30

Leu Ser Glu Leu Gly Ala Thr Phe Lys Val Val Glu Leu Asp Thr Glu

```
                35                  40                  45
Ser Asp Gly Ala Asp Leu Gln Ser Ala Leu Ala Gly Trp Thr Gly Gln
 50                  55                  60

Arg Thr Val Pro Asn Val Phe Ile Gly Gly Lys His Ile Gly Gly Cys
 65                  70                  75                  80

Asp Thr Ala Thr Ala Leu His Ser Asp Gly Lys Leu Val Pro Leu Leu
                 85                  90                  95

Thr Glu Ala Gly Ala Ile Thr Ser Ser Asn Glu Gly Ser Ser Val
                100                 105                 110

Thr Cys

<210> SEQ ID NO 93
<211> LENGTH: 111
<212> TYPE: PRT
<213> ORGANISM: Arabis alpina
<220> FEATURE:
<221> NAME/KEY: MISC_FEATURE
<222> LOCATION: (1)..(111)
<223> OTHER INFORMATION: glutaredoxin

<400> SEQUENCE: 93

Met Pro Met Gln Lys Ala Lys Glu Leu Val Ser Ser Asn Ser Val Val
 1               5                  10                  15

Val Phe Ser Lys Ser Tyr Cys Pro Tyr Cys Val Arg Val Lys Glu Leu
                20                  25                  30

Leu Gln Gln Leu Gly Ala Thr Phe Lys Ala Ile Glu Leu Asp Asn Glu
                35                  40                  45

Ser Asp Gly Ala Ala Val Gln Ser Ala Leu Gly Glu Trp Thr Gly Gln
 50                  55                  60

Arg Thr Val Pro Asn Val Phe Ile Gly Gly Lys His Ile Gly Gly Cys
 65                  70                  75                  80

Asp Ala Thr Thr Asn Leu His Arg Asp Gly Lys Leu Val Pro Leu Leu
                 85                  90                  95

Thr Glu Ala Gly Ala Val Ala Ala Lys Ser Gly Thr Thr Ser Ala
                100                 105                 110

<210> SEQ ID NO 94
<211> LENGTH: 119
<212> TYPE: PRT
<213> ORGANISM: Zostera marina
<220> FEATURE:
<221> NAME/KEY: MISC_FEATURE
<222> LOCATION: (1)..(119)
<223> OTHER INFORMATION: glutaredoxin

<400> SEQUENCE: 94

Met Gly Gly Met Leu Ser Ser Lys Ser Thr Pro Glu Gly Arg Ala Met
 1               5                  10                  15

Ala Leu Thr Lys Ala Lys Glu Ile Val Ser Ser Asn Gly Val Val Val
                20                  25                  30

Phe Ser Lys Ser Tyr Cys Pro Tyr Cys Asn Arg Val Lys Asp Leu Phe
                35                  40                  45

Ser Lys Leu Gly Val Thr Tyr Lys Val Val Glu Leu Asp Val Glu Ser
 50                  55                  60

Asp Gly Ser Asp Met Gln Ser Ala Leu Ala Glu Trp Ser Gly Gln Arg
 65                  70                  75                  80

Thr Val Pro Asn Val Phe Ile Lys Glu Thr His Ile Gly Gly Cys Asp
                 85                  90                  95
```

Ser Val Met Gly Ile His Lys Asp Gly Lys Leu Ile Pro Leu Leu Thr
            100                 105                 110

Asp Ala Gly Ala Ile Ser Val
            115

<210> SEQ ID NO 95
<211> LENGTH: 108
<212> TYPE: PRT
<213> ORGANISM: Arachis ipaensis
<220> FEATURE:
<221> NAME/KEY: MISC_FEATURE
<222> LOCATION: (1)..(108)
<223> OTHER INFORMATION: glutaredoxin

<400> SEQUENCE: 95

Met Ala Leu Pro Lys Ala Lys Glu Ile Val Ser Ser Asn Pro Val Val
1               5                   10                  15

Val Phe Ser Lys Thr Tyr Cys Pro Phe Cys Val Glu Val Lys Gln Leu
                20                  25                  30

Phe Thr Lys Leu Gly Val Thr Val Lys Val Ile Glu Leu Asn Thr Glu
            35                  40                  45

Ser Asp Gly Ser Glu Ile Gln Ser Ala Leu Ala Glu Trp Thr Gly Gln
50                  55                  60

Arg Thr Val Pro Asn Val Phe Ile Gly Gly Asn His Ile Gly Gly Cys
65                  70                  75                  80

Asp Ala Thr Thr Asn Leu His Ser Gln Gly Lys Leu Val Pro Leu Leu
                85                  90                  95

Thr Ser Ala Gly Thr Thr Val Ala Ser Ala Ser Gly
            100                 105

<210> SEQ ID NO 96
<211> LENGTH: 107
<212> TYPE: PRT
<213> ORGANISM: Cajanus cajan
<220> FEATURE:
<221> NAME/KEY: MISC_FEATURE
<222> LOCATION: (1)..(107)
<223> OTHER INFORMATION: glutaredoxin

<400> SEQUENCE: 96

Met Ala Leu Pro Lys Ala Lys Glu Ile Val Ser Ala Asn Ser Val Val
1               5                   10                  15

Val Phe Ser Lys Thr Tyr Cys Pro Phe Cys Val Glu Val Lys Asn Leu
                20                  25                  30

Phe Gly Asn Leu Gly Ala Thr Tyr Lys Val Val Glu Leu Asp Thr Glu
            35                  40                  45

Ala Asp Gly Ser Glu Ile Gln Thr Ala Leu Lys Glu Trp Thr Gly Gln
50                  55                  60

Arg Thr Val Pro Asn Val Phe Ile Gly Gly Lys His Ile Gly Gly Cys
65                  70                  75                  80

Asp Ser Thr Thr Ala Leu His Asn Gln Gly Lys Leu Leu Pro Leu Leu
                85                  90                  95

Glu Ser Thr Gly Ala Val Ala Lys Ser Thr Ala
            100                 105

<210> SEQ ID NO 97
<211> LENGTH: 107
<212> TYPE: PRT
<213> ORGANISM: Theobroma cacao
<220> FEATURE:
<221> NAME/KEY: MISC_FEATURE
<222> LOCATION: (1)..(107)
<223> OTHER INFORMATION: glutaredoxin

<400> SEQUENCE: 97

Met Ala Leu Pro Lys Ala Lys Glu Val Val Ser Ala Asn Pro Val Val
1               5                   10                  15

Val Phe Ser Lys Ser Tyr Cys Pro Tyr Cys Val Asn Val Lys Gln Leu
            20                  25                  30

Leu Gln Gln Leu Gly Ala Ser Phe Lys Ala Ile Glu Leu Asn Asn Glu
        35                  40                  45

Ser Asp Gly Ser Glu Ile Gln Ala Ala Leu Ala Glu Trp Thr Gly Leu
    50                  55                  60

Arg Thr Val Pro Asn Val Phe Ile Gly Gly Lys His Ile Gly Gly Cys
65                  70                  75                  80

Asp Val Thr Thr Thr Leu His Glu Glu Gly Lys Leu Ile Pro Leu Leu
                85                  90                  95

Thr Glu Ala Gly Ala Val Ala Lys Pro Ser Gly
            100                 105

<210> SEQ ID NO 98
<211> LENGTH: 107
<212> TYPE: PRT
<213> ORGANISM: Cicer arietinum
<220> FEATURE:
<221> NAME/KEY: MISC_FEATURE
<222> LOCATION: (1)..(107)
<223> OTHER INFORMATION: glutaredoxin

<400> SEQUENCE: 98

Met Ala Leu Pro Lys Ala Lys Glu Ile Val Ser Ser Asn Pro Val Val
1               5                   10                  15

Val Phe Ser Lys Ser Tyr Cys Pro Phe Cys Val Gln Val Lys Lys Leu
            20                  25                  30

Phe Thr Asn Leu Gly Val Thr Phe Lys Ala Ile Glu Leu Asp Ser Glu
        35                  40                  45

Ser Asp Gly Ser Glu Ile Gln Gly Ala Leu Ala Glu Trp Thr Gly Gln
    50                  55                  60

Arg Thr Val Pro Ser Val Phe Ile Gly Gly Asn His Ile Gly Gly Cys
65                  70                  75                  80

Asp Ala Thr Thr Asn Leu His Asn Gln Gly Lys Leu Val Ser Leu Leu
                85                  90                  95

Ala Ser Ala Gly Ala Val Ser Gly Ser Thr Ser
            100                 105

<210> SEQ ID NO 99
<211> LENGTH: 107
<212> TYPE: PRT
<213> ORGANISM: Glycine max
<220> FEATURE:
<221> NAME/KEY: MISC_FEATURE
<222> LOCATION: (1)..(107)
<223> OTHER INFORMATION: glutaredoxin

<400> SEQUENCE: 99

Met Ala Leu Pro Lys Ala Lys Glu Ile Val Ser Ser Asn Ser Val Val
1               5                   10                  15

Val Phe Ser Lys Thr Tyr Cys Pro Phe Cys Val Asp Val Lys Lys Leu
            20                  25                  30

Phe Gly Asp Leu Gly Ala Asn Tyr Lys Ala Ile Glu Leu Asp Thr Glu
        35                  40                  45

```
Ser Asp Gly Lys Glu Leu Gln Ala Ala Leu Val Glu Trp Thr Asp Gln
 50                  55                  60

Arg Thr Val Pro Asn Val Phe Ile Gly Gly Asn His Ile Gly Gly Cys
 65                  70                  75                  80

Asp Ser Thr Thr Ala Leu His Thr Gln Gly Lys Leu Val Pro Leu Leu
                 85                  90                  95

Ile Ser Ala Gly Ala Val Ala Lys Ser Thr Ala
            100                 105

<210> SEQ ID NO 100
<211> LENGTH: 125
<212> TYPE: PRT
<213> ORGANISM: Elaeis guineensis
<220> FEATURE:
<221> NAME/KEY: MISC_FEATURE
<222> LOCATION: (1)..(125)
<223> OTHER INFORMATION: glutaredoxin

<400> SEQUENCE: 100

Met Gly Gly Leu Trp Ser Ser Ser Val Gly Ser Lys Glu Glu Gln
 1               5                  10                  15

Gly Glu Met Ala Leu Ala Lys Ala Lys Glu Leu Val Ser Ser Asn Pro
                 20                  25                  30

Val Met Val Phe Ser Lys Ser Tyr Cys Pro Tyr Cys Thr Arg Val Lys
                 35                  40                  45

Gln Leu Leu Ser Gln Leu Gly Ala Ser Tyr Lys Val Ile Glu Leu Asp
 50                  55                  60

Val Glu Ser Asp Gly Ser Glu Val Gln Ser Ala Leu Ala Glu Trp Thr
 65                  70                  75                  80

Gly Leu Arg Thr Val Pro Asn Val Phe Ile Gly Gly Asn His Ile Gly
                 85                  90                  95

Gly Cys Asp Asn Val Met Glu Arg His Asn Gly Gly Lys Leu Val Pro
                100                 105                 110

Leu Leu Thr Glu Ala Gly Ala Leu Ala Ser Pro Ala Ala
                115                 120                 125

<210> SEQ ID NO 101
<211> LENGTH: 107
<212> TYPE: PRT
<213> ORGANISM: Prunus mume
<220> FEATURE:
<221> NAME/KEY: MISC_FEATURE
<222> LOCATION: (1)..(107)
<223> OTHER INFORMATION: glutaredoxin

<400> SEQUENCE: 101

Met Ala Leu Thr Lys Ala Lys Glu Ile Val Ser Ser Asn Ser Val Val
 1               5                  10                  15

Val Phe Ser Lys Thr Tyr Cys Pro Tyr Cys Val Ser Val Lys Gln Leu
                 20                  25                  30

Leu Thr Gln Leu Gly Ala Lys Phe Lys Ala Ile Glu Leu Asp Thr Glu
                 35                  40                  45

Ser Asp Gly Ala Gln Ile Gln Ser Ala Leu Gly Glu Trp Ser Gly Gln
 50                  55                  60

Arg Thr Val Pro Asn Val Phe Ile Gly Gly Asn His Ile Gly Gly Cys
 65                  70                  75                  80

Asp Thr Thr Thr Ala Leu His Lys Glu Gly Lys Leu Val Pro Leu Leu
                 85                  90                  95
```

Ser Gln Ala Gly Ala Val Thr Lys Thr Ser Ala
            100                 105

<210> SEQ ID NO 102
<211> LENGTH: 104
<212> TYPE: PRT
<213> ORGANISM: Fritillaria agrestis
<220> FEATURE:
<221> NAME/KEY: MISC_FEATURE
<222> LOCATION: (1)..(104)
<223> OTHER INFORMATION: glutaredoxin

<400> SEQUENCE: 102

Met Ala Leu Ala Lys Ala Lys Asp Leu Val Ala Ser Asn Pro Val Val
1               5                   10                  15

Val Phe Ser Lys Ser Tyr Cys Pro Tyr Cys Ile Arg Val Lys Glu Leu
                20                  25                  30

Leu Val Lys Leu Lys Ala Thr Tyr Lys Val Ile Glu Leu Asp Leu Glu
            35                  40                  45

Ser Asp Gly Ser Ala Ile Gln Ala Ala Leu Ala Glu Trp Thr Gly Gln
    50                  55                  60

Arg Thr Val Pro Asn Val Phe Ile Gly Gly Lys His Ile Gly Gly Cys
65                  70                  75                  80

Asp Lys Thr Met Glu Leu Tyr Asn Ser Gly Lys Leu Gln Pro Leu Leu
                85                  90                  95

Val Glu Ala Gly Ala Leu Ala Ala
            100

US 11,359,207 B2

INCREASING PLANT GROWTH AND YIELD BY USING A GLUTAREDOXIN

CROSS-REFERENCE TO RELATED APPLICATIONS

This application is a national stage filing under 35 U.S.C. 371 of PCT/IB2018/056128 filed Aug. 15, 2018, which International Application was published by the International Bureau in English on Feb. 21, 2019, and application claims priority from U.S. Provisional Patent Application No. 62/546,673, filed Aug. 17, 2017, which applications are hereby incorporated in their entirety by reference in this application.

FIELD OF THE INVENTION

The invention is drawn to compositions and methods for increasing plant growth and yield through expression of a glutaredoxin gene in a plant.

BACKGROUND OF THE INVENTION

The ever-increasing world population and the dwindling supply of arable land available for agriculture fuels research towards developing plants with increased biomass and yield. Conventional means for crop and horticultural improvements utilize selective breeding techniques to identify plants having desirable characteristics. However, such selective breeding techniques have several drawbacks, namely that these techniques are typically labor intensive and result in plants that often contain heterogeneous genetic components that may not always result in the desirable trait being passed on from parent plants. Advances in molecular biology provide means to precisely modify the germplasm of plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

Traits of interest include plant biomass and yield. Yield is normally defined as the measurable produce of economic value from a crop. This may be defined in terms of quantity and/or quality. Yield is directly dependent on several factors, for example, the number and size of the organs, plant architecture (for example, the number of branches), seed production, leaf senescence and more. Root development, nutrient uptake, stress tolerance, photosynthetic carbon assimilation rates, and early vigor may also be important factors in determining yield. Optimizing the abovementioned factors may therefore contribute to increasing crop yield.

An increase in seed yield is a particularly important trait since the seeds of many plants are important for human and animal consumption. Crops such as corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain. An increase in plant biomass is important for forage crops like alfalfa, silage corn and hay. Many genes are involved in the metabolic pathways that contribute to plant growth and development. Modulating the expression of one or more such genes in a plant can produce a plant with improved growth and development relative to a control plant, but often can produce a plant with impaired growth and development relative to a control plant. Therefore, methods to improve plant growth and development are needed.

SUMMARY OF THE INVENTION

Compositions and methods for regulating gene expression in a plant are provided. The methods increase plant growth resulting in higher crop yield. Such methods include increasing the expression of at least one glutaredoxin gene in a plant of interest. The invention also encompasses constructs comprising a promoter that drives expression in a plant cell operably linked to a glutaredoxin coding sequence. Compositions further comprise plants, plant seeds, plant organs, plant cells, and other plant parts that have increased expression of a glutaredoxin sequence. The invention includes methods that can be utilized to increase expression of a glutaredoxin gene in a plant. Such glutaredoxin gene may be a native sequence or alternatively, may be a sequence that is heterologous to the plant of interest.

Embodiments of the invention include:
1. A method for increasing crop yield comprising transforming a plant with at least one glutaredoxin protein-encoding sequence.
2. The method of embodiment 1, wherein said glutaredoxin protein-encoding sequence comprises a sequence selected from the group of SEQ ID NOs:1 and 2, or encodes a protein selected from the group of SEQ ID NOs:3 and 15-102.
3. The method of embodiment 1, wherein said glutaredoxin protein-encoding sequence encodes a protein with at least 80%, 90%, 95%, 96%, 97%, 98%, or 99% sequence identity to a sequence selected from the group of SEQ ID NOs:3 and 15-102, and that has glutaredoxin function.
4. The method of embodiment 1, wherein said glutaredoxin protein-encoding sequence encodes a protein with at least 80%, 85%, 90%, 95%, 96%, 97%, 98%, or 99% sequence positives relative to a sequence selected from the group of SEQ ID NOs:3 and 15-102, and that has glutaredoxin function.
5. A plant having stably incorporated into its genome a promoter that drives expression in a plant operably linked to a glutaredoxin protein-encoding sequence, wherein said promoter is heterologous to said glutaredoxin protein-encoding sequence.
6. The plant of embodiment 5, wherein said glutaredoxin protein-encoding sequence comprises a sequence selected from the group of SEQ ID NOs:1 and 2, or encodes a protein selected from the group of SEQ ID NOs:3 and 15-102.
7. The plant of embodiment 5, wherein said glutaredoxin protein-encoding sequence encodes a protein with at least 80%, 85%, 90%, 95%, 96%, 97%, 98%, or 99% sequence identity to a sequence selected from the group of SEQ ID NOs:3 and 15-102, and that has glutaredoxin function.

8. The plant of embodiment 5, wherein said glutaredoxin protein-encoding sequence encodes a protein with at least 80%, 85%, 90%, 95%, 96%, 97%, 98%, or 99% sequence positives relative to a sequence selected from the group of SEQ ID NOs:3 and 15-102, and that has glutaredoxin function.
9. Transformed seed of any one of the plants of embodiments 5-8.
10. The plant of any one of embodiments 5-8 wherein said plant is a monocot.
11. The plant of embodiment 10 wherein said plant is from the genus *Zea, Oryza, Triticum, Sorghum, Secale, Eleusine, Setaria, Saccharum, Miscanthus, Panicum, Pennisetum, Megathyrsus, Cocos, Ananas, Musa, Elaeis, Avena,* or *Hordeum*.
12. The plant of any one of embodiments 5-8 wherein said plant is a dicot.
13. The plant of embodiment 12 wherein said plant is from the genus *Glycine, Brassica, Medicago, Helianthus, Carthamus, Nicotiana, Solanum, Gossypium, Ipomoea, Manihot, Coffea, Citrus, Theobroma, Camellia, Persea, Ficus, Psidium, Mangifera, Olea, Carica, Anacardium, Macadamia, Prunus, Beta, Populus,* or *Eucalyptus*.
14. The plant of any one of embodiments 5-8 wherein said plant exhibits increased growth relative to a control plant.
15. The plant of any one of embodiments 5-8 wherein said plant exhibits increased biomass yield relative to a control plant.
16. The plant of any one of embodiments 5-8 wherein said plant exhibits increased seed yield relative to a control plant.
17. The method of any one of embodiments 1-4, wherein said glutaredoxin protein-encoding sequence is expressed from a bundle sheath cell-preferred promoter.
18. The method of embodiment 17, wherein said bundle sheath cell-preferred promoter comprises SEQ ID NO:10.
19. The plant of any one of embodiments 5-8, wherein said promoter that drives expression in a plant is a bundle sheath cell-preferred promoter.
20. The plant of embodiment 19, wherein said bundle sheath cell-preferred promoter comprises SEQ ID NO:10.
21. The plant of embodiment 5 having stably incorporated into its genome a second promoter that drives expression in a plant operably linked to a second protein-encoding sequence, wherein said second promoter is heterologous to said second protein-encoding sequence.
22. A DNA construct comprising, in operable linkage,
    a. A promoter that is functional in a plant cell and,
    b. A nucleic acid sequence encoding a glutaredoxin protein.
23. The DNA construct of embodiment 22, wherein said nucleic acid sequence encoding a glutaredoxin protein comprises a sequence selected from the group of SEQ ID NOs:1 and 2, or encodes a protein selected from the group consisting of SEQ ID NOs:3 and 15-102.
24. The DNA construct of embodiment 22 or 23, wherein said nucleic acid sequence encoding a glutaredoxin protein encodes a protein with at least 80%, 85%, 90%, 95%, 96%, 97%, 98%, or 99% sequence identity to a sequence selected from the group of SEQ ID NOs:3 and 15-102, and that glutaredoxin function.
25. The DNA construct of embodiment 22 or 23, wherein said nucleic acid sequence encoding a glutaredoxin protein encodes a protein with at least 80%, 85%, 90%, 95%, 96%, 97%, 98%, or 99% sequence positives relative to a sequence selected from the group of SEQ ID NOs:3 and 15-102, and that has glutaredoxin function.
26. The DNA construct of embodiment 22 or 23, wherein said promoter that is functional in a plant cell comprises SEQ ID NO:10.
27. The DNA construct of any one of embodiments 22-26, wherein said promoter is heterologous to said nucleic acid sequence encoding a glutaredoxin protein.
28. A method for increasing crop yield comprising modulating the expression of at least one glutaredoxin protein-encoding sequence in a plant.
29. The method of embodiment 28 wherein said modulating the expression comprises increasing the expression of at least one glutaredoxin protein-encoding sequence in a plant.
30. The method of embodiment 29, wherein said increasing the expression comprises increasing the activity of a native glutaredoxin sequence in said plant or increasing activity of a native glutaredoxin protein-encoding sequence in said plant.
31. The plant of any one of embodiments 5-8, wherein said promoter that drives expression in a plant is active in leaf tissue.
32. The DNA construct of any one of embodiments 22-27, wherein said promoter that is functional in a plant cell is active in leaf tissue.

DETAILED DESCRIPTION OF THE INVENTION

Compositions and methods for increasing crop biomass and yield are provided. The methods include increasing the expression of at least one glutaredoxin gene in a plant of interest. Crop yield is an extremely complex trait that results from the growth of a crop plant through all stages of its development and allocation of plant resources to the harvestable portions of the plant. In some crops including but not limited to maize and soybean, the primary harvestable portions may include seeds, with secondary applications from the remainder of the biomass (e.g., leaves and stems). In other crops including but not limited to sugarcane and alfalfa, the primary harvestable portions of the plant consist of the stems or entire above-ground portion of the plant. In other crops including but not limited to potato and carrot, the primary harvestable portions of the plant are found belowground. Regardless of the harvested portion(s) of the crop plant, the accumulation of harvestable biomass results from plant growth and allocation of photosynthetically fixed carbon to the harvested portion(s) of the plant. Plant growth may be manipulated by modulating the expression of one or more plant genes. This modulation can alter the function of one or more metabolic pathways that contributes to plant growth and accumulation of harvestable biomass.

Methods of the invention include the manipulation of plant growth for increased yield through modulation of the expression of one or more genes encoding a glutaredoxin protein. In a preferred embodiment, the expression of a glutaredoxin protein-encoding gene is upregulated relative to glutaredoxin expression levels in a control plant, resulting in increased harvestable biomass in plants with increased glutaredoxin expression relative to control plants. Any methods for increasing the activity or expression of a glutaredoxin protein-encoding sequence in a plant are encompassed by the present invention.

The compositions of the invention include constructs comprising the coding sequences set forth in SEQ ID NOs:1 and 2 or encoding a protein selected from the group of SEQ ID NOs:3 and 15-102 or variants thereof, operably linked to a promoter that is functional in a plant cell. By "promoter" is intended to mean a regulatory region of DNA that is capable of driving expression of a sequence in a plant or plant cell. It is recognized that having identified the glutaredoxin protein sequences disclosed herein, it is within the state of the art to isolate and identify additional glutaredoxin protein sequences and nucleotide sequences encoding glutaredoxin protein sequences, for instance through BLAST searches, PCR assays, and the like.

The coding sequences of the present invention, when assembled within a DNA construct such that a promoter is operably linked to the coding sequence of interest, enable expression and accumulation of glutaredoxin protein in the cells of a plant stably transformed with this DNA construct. "Operably linked" is intended to mean a functional linkage between two or more elements. For example, an operable linkage between a promoter of the present invention and a heterologous nucleotide of interest is a functional link that allows for expression of the heterologous nucleotide sequence of interest. Operably linked elements may be contiguous or non-contiguous. When used to refer to the joining of two protein coding regions, by operably linked is intended that the coding regions are in the same reading frame. The cassette may additionally contain at least one additional gene to be co-transformed into the plant. Alternatively, the additional gene(s) can be provided on multiple expression cassettes or DNA constructs. The expression cassette may additionally contain selectable marker genes.

In this manner, the nucleotide sequences encoding the glutaredoxin proteins of the invention are provided in expression cassettes or expression constructs along with a promoter sequence of interest, typically a heterologous promoter sequence, for expression in the plant of interest. By "heterologous promoter sequence" is intended to mean a sequence that is not naturally operably linked with the glutaredoxin protein-encoding nucleotide sequence. While the glutaredoxin protein-encoding nucleotide sequence and the promoter sequence are heterologous to each other, either the glutaredoxin protein-encoding nucleotide sequence or the heterologous promoter sequence may be homologous, or native, or heterologous, or foreign, to the plant host. It is recognized that the promoter may also drive expression of its homologous or native nucleotide sequence. In this case, the transformed plant will have a change in phenotype.

Fragments and variants of the polynucleotides and amino acid sequences of the present invention may also be expressed by promoters that are operable in plant cells. By "fragment" is intended a portion of the polynucleotide or a portion of the amino acid sequence. "Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. Generally, variants of a particular polynucleotide of the invention will have at least about 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein. Fragments and variants of the polynucleotides disclosed herein can encode proteins that retain glutaredoxin function.

"Variant" amino acid or protein is intended to mean an amino acid or protein derived from the native amino acid or protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins encompassed by the present invention are biologically active, that is they continue to possess the desired biological activity of the native protein, such as oxidation by a substrate and non-enzymatic reduction by glutathione. Biologically active variants of a native polypeptide will have at least about 80%, 85%, 90%, 91%, 92%, 93%, 94%, 95%, 96%, 97%, 98%, 99% or more sequence identity to the amino acid sequence for the native sequence as determined by sequence alignment programs and parameters described herein. In some embodiments, the variant polypeptide sequences will comprise conservative amino acid substitutions. The number of such conservative amino acid substitutions, summed with the number of amino acid identities, can be used to calculate the sequence positives when this sum is divided by the total number of amino acids in the sequence of interest. Sequence positive calculations are performed on the NCBI BLAST server that can be accessed on the world wide web at blast.ncbi.nlm.nih.gov/Blast.cgi. A biologically active variant of a protein of the invention may differ from that protein by as few as 1-15 amino acid residues, as few as 1-10, such as 6-10, as few as 5, as few as 4, 3, 2, or even 1 amino acid residue.

Amino acids can be generally categorized as aliphatic, hydroxyl or sulfur/selenium-containing, cyclic, aromatic, basic, or acidic and their amide. Without being limited by theory, conservative amino acid substitutions may be preferable in some cases to non-conservative amino acid substitutions for the generation of variant protein sequences, as conservative substitutions may be more likely than non-conservative substitutions to allow the variant protein to retain its biological activity. Polynucleotides encoding a polypeptide having one or more amino acid substitutions in the sequence are contemplated within the scope of the present invention. Table 1 below provides a listing of examples of amino acids belong to each class.

TABLE 1

| Classes of Amino Acids | |
| --- | --- |
| Amino Acid Class | Example Amino Acids |
| Aliphatic | Gly, Ala, Val, Leu, Ile |
| Hydroxyl or sulfur/selenium-containing | Ser, Cys, Thr, Met, Sec |
| Cyclic | Pro |
| Aromatic | Phe, Tyr, Trp |
| Basic | His, Lys, Arg |
| Acidic and their Amide | Asp, Glu, Asn, Gln |

Variant sequences may also be identified by analysis of existing databases of sequenced genomes. In this manner, corresponding sequences can be identified and used in the methods of the invention.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Such genes and coding regions can be codon optimized for expression in a plant of interest. A "codon-optimized gene" is a gene having its frequency of codon usage designed to mimic the frequency of preferred codon usage of the host cell. Nucleic acid molecules can be codon optimized, either wholly or in part. Because any one amino acid (except for methionine and tryptophan) is encoded by a number of codons, the sequence of the nucleic acid molecule may be changed without changing the encoded amino acid. Codon optimization is when one or more codons are altered at the nucleic acid level such that the amino acids are not changed but expression in a particular host organism is increased. Those having ordinary skill in the art will recognize that codon tables and other references providing preference information for a wide range of organisms are available in the art (see, e.g., Zhang et al. (1991) *Gene* 105:61-72; Murray et al. (1989) *Nucl. Acids Res.* 17:477-508). Methodology for optimizing a nucleotide sequence for expression in a plant is provided, for example, in U.S. Pat. No. 6,015,891, and the references cited therein, as well as in WO 2012/142,371, and the references cited therein.

The nucleotide sequences of the invention may be used in recombinant polynucleotides. A "recombinant polynucleotide" comprises a combination of two or more chemically linked nucleic acid segments which are not found directly joined in nature. By "directly joined" is intended the two nucleic acid segments are immediately adjacent and joined to one another by a chemical linkage. In specific embodiments, the recombinant polynucleotide comprises a polynucleotide of interest or active variant or fragment thereof such that an additional chemically linked nucleic acid segment is located either 5', 3' or internal to the polynucleotide of interest. Alternatively, the chemically-linked nucleic acid segment of the recombinant polynucleotide can be formed by deletion of a sequence. The additional chemically linked nucleic acid segment or the sequence deleted to join the linked nucleic acid segments can be of any length, including for example, 1, 2, 3, 4, 5, 6, 7, 8, 9, 10, 15, 20 or greater nucleotides. Various methods for making such recombinant polynucleotides are disclosed herein, including, for example, by chemical synthesis or by the manipulation of isolated segments of polynucleotides by genetic engineering techniques. In specific embodiments, the recombinant polynucleotide can comprise a recombinant DNA sequence or a recombinant RNA sequence. A "fragment of a recombinant polynucleotide" comprises at least one of a combination of two or more chemically linked amino acid segments which are not found directly joined in nature.

By "altering" or "modulating" the expression level of a gene is intended that the expression of the gene is upregulated or downregulated. It is recognized that in some instances, plant growth and yield are increased by increasing the expression levels of one or more genes encoding glutaredoxin proteins, i.e. upregulating expression. Likewise, in some instances, plant growth and yield may be increased by decreasing the expression levels of one or more genes encoding glutaredoxin proteins, i.e. downregulating expression. Thus, the invention encompasses the upregulation or downregulation of one or more genes encoding glutaredoxin proteins. Further, the methods include the upregulation of at least one gene encoding a glutaredoxin protein and the downregulation of at least one gene encoding a second glutaredoxin protein in a plant of interest. By modulating the concentration and/or activity of at least one of the genes encoding a glutaredoxin protein in a transgenic plant is intended that the concentration and/or activity is increased or decreased by at least about 1%, about 5%, about 10%, about 20%, about 30%, about 40%, about 50%, about 60%, about 70%, about 80%, or about 90% or greater relative to a native control plant, plant part, or cell which did not have the sequence of the invention introduced.

It is recognized that the expression levels of the genes encoding glutaredoxin proteins of the present invention can be controlled by the use of one or more promoters that are functional in a plant cell. The expression level of the glutaredoxin protein-encoding gene of interest may be measured directly, for example, by assaying for the level of the glutaredoxin gene transcript or of the encoded protein in the plant. Methods for such assays are well-known in the art. For example, Northern blotting or quantitative reverse transcriptase-PCR (qRT-PCR) may be used to assess transcript levels, while western blotting, ELISA assays, or enzyme assays may be used to assess protein levels. Glutaredoxin function can be assessed by, for example, commercial fluorescence assays (Cayman Chemical, Ann Arbor, Mich.).

A "subject plant or plant cell" is one in which genetic alteration, such as transformation, has been effected as to a glutaredoxin protein-encoding gene of interest, or is a plant or plant cell which is descended from a plant or cell so altered and which comprises the alteration. A "control" or "control plant" or "control plant cell" provides a reference point for measuring changes in phenotype of the subject plant or plant cell. Thus, the expression levels of a glutaredoxin protein-encoding gene of interest are higher or lower than those in the control plant depending on the methods of the invention.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

While the invention is described in terms of transformed plants, it is recognized that transformed organisms of the invention also include plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

To downregulate expression of a glutaredoxin protein-encoding gene of interest, antisense constructions, complementary to at least a portion of the messenger RNA (mRNA) for the sequences of a gene of interest, particularly a gene encoding a glutaredoxin protein of interest can be constructed. Antisense nucleotides are designed to hybridize with the corresponding mRNA. Modifications of the antisense sequences may be made as long as the sequences hybridize to and interfere with expression of the corresponding mRNA. In this manner, antisense constructions having 70%, optimally 80%, more optimally 85%, 90%, 95% or greater sequence identity to the corresponding sequences to be silenced may be used. Furthermore, portions of the antisense nucleotides may be used to disrupt the expression of the target gene.

The polynucleotides of the invention can be used to isolate corresponding sequences from other plants. In this manner, methods such as PCR, hybridization, and the like can be used to identify such sequences based on their sequence homology or identity to the sequences set forth herein. Sequences isolated based on their sequence identity to the entire sequences set forth herein or to variants and fragments thereof are encompassed by the present invention.

Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that have transcription activation or enhancer activities and which share at least 75% sequence identity to the sequences disclosed herein, or to variants or fragments thereof, are encompassed by the present invention.

Variant sequences can be isolated by PCR. Methods for designing PCR primers and PCR cloning are generally known in the art and are disclosed in Sambrook et al. (1989) Molecular Cloning: A Laboratory Manual (2d ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York).

Variant sequences may also be identified by analysis of existing databases of sequenced genomes. In this manner, corresponding sequences encoding glutaredoxin proteins can be identified and used in the methods of the invention. The variant sequences will retain the biological activity of a glutaredoxin protein (i.e., oxidation by substrates and non-enzymatic reduction by glutathione). The present invention shows that, unexpectedly, certain novel expression strategies for glutaredoxin protein overexpression can lead to increased biomass and seed yield.

The expression cassette will include in the 5'-3' direction of transcription, a transcriptional and translational initiation region, a polynucleotide encoding a glutaredoxin protein of the present invention, and a transcriptional and translational termination region (i.e., termination region) functional in plants.

A number of promoters may be used in the practice of the invention. The polynucleotides encoding a glutaredoxin protein of the invention may be expressed from a promoter with a constitutive expression profile. Constitutive promoters include the CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like.

Polynucleotides of the invention encoding glutaredoxin proteins of the invention may be expressed from tissue-preferred promoters. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Leaf-preferred promoters are also known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6): 1129-1138; and Matsuoka et al. (1993) *Proc. Natl. Acad. Sci. USA* 90(20):9586-9590.

Developmentally-regulated promoters may be desirable for the expression of a polynucleotide encoding a glutaredoxin protein. Such promoters may show a peak in expression at a particular developmental stage. Such promoters have been described in the art, e.g., U.S. 62/029,068; Gan and Amasino (1995) *Science* 270: 1986-1988; Rinehart et al. (1996) *Plant Physiol* 112: 1331-1341; Gray-Mitsumune et al. (1999) *Plant Mol Biol* 39: 657-669; Beaudoin and Rothstein (1997) *Plant Mol Biol* 33: 835-846; Genschik et al. (1994) *Gene* 148: 195-202, and the like.

Promoters that are induced following the application of a particular biotic and/or abiotic stress may be desirable for the expression of a polynucleotide encoding a glutaredoxin protein. Such promoters have been described in the art, e.g., Yi et al. (2010) *Planta* 232: 743-754; Yamaguchi-Shinozaki and Shinozaki (1993) *Mol Gen Genet* 236: 331-340; U.S. Pat. No. 7,674,952; Rerksiri et al. (2013) *Sci World J* 2013: Article ID 397401; Khurana et al. (2013) *PLoS One* 8: e54418; Tao et al. (2015) *Plant Mol Biol Rep* 33: 200-208, and the like.

Cell-preferred promoters may be desirable for the expression of a polynucleotide encoding a glutaredoxin protein. Such promoters may preferentially drive the expression of a downstream gene in a particular cell type such as a mesophyll or a bundle sheath cell. Such cell-preferred promoters have been described in the art, e.g., Viret et al. (1994) *Proc Natl Acad USA* 91: 8577-8581; U.S. Pat. Nos. 8,455,718; 7,642,347; Sattarzadeh et al. (2010) *Plant Biotechnol J* 8: 112-125; Engelmann et al. (2008) *Plant Physiol* 146: 1773-1785; Matsuoka et al. (1994) *Plant J* 6: 311-319, and the like.

It is recognized that a specific, non-constitutive expression profile may provide an improved plant phenotype relative to constitutive expression of a gene or genes of interest. For instance, many plant genes are regulated by light conditions, the application of particular stresses, the circadian cycle, or the stage of a plant's development. These expression profiles may be important for the function of the gene or gene product in planta. One strategy that may be used to provide a desired expression profile is the use of synthetic promoters containing cis-regulatory elements that drive the desired expression levels at the desired time and place in the plant. Cis-regulatory elements that can be used to alter gene expression in planta have been described in the scientific literature (Vandepoele et al. (2009) *Plant Physiol* 150: 535-546; Rushton et al. (2002) *Plant Cell* 14: 749-762). Cis-regulatory elements may also be used to alter promoter expression profiles, as described in Venter (2007) *Trends Plant Sci* 12: 118-124.

Plant terminators are known in the art and include those available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

As indicated, the nucleotides encoding glutaredoxin proteins of the present invention can be used in expression cassettes to transform plants of interest. Transformation protocols as well as protocols for introducing polypeptides or polynucleotide sequences into plants may vary depending on the type of plant or plant cell, i.e., monocot or dicot, targeted for transformation. The term "transform" or "transformation" refers to any method used to introduce polypeptides or polynucleotides into plant cells. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in Plant Cell, Tissue, and Organ Culture: Fundamental Methods, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in The Experimental Manipulation of Ovule Tissues, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference. "Stable transformation" is intended to mean that the nucleotide construct introduced into a plant integrates into the genome of the plant and is capable of being inherited by the progeny thereof.

The cells that have been transformed may be grown into plants in accordance with conventional ways. See, for example, McCormick et al. (1986) *Plant Cell Reports* 5:81-84. In this manner, the present invention provides transformed seed (also referred to as "transgenic seed") having a polynucleotide of the invention, for example, an expression cassette of the invention, stably incorporated into their genome.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), camelina (*Camelina sativa*), millet (e.g., pearl millet (*Pennisetum glaucum*), proso millet (*Panicum miliaceum*), foxtail millet (*Setaria* italica), finger millet (*Eleusine coracana*)), sunflower (*Helianthus annuus*), quinoa (*Chenopodium quinoa*), chicory (*Cichorium intybus*), lettuce (*Lactuca sativa*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oil palm (*Elaeis guineensis*), poplar (*Populus* spp.), eucalyptus (*Eucalyptus* spp.), oats (*Avena sativa*), barley (*Hordeum vulgare*), vegetables, ornamentals, and conifers.

In one embodiment, a construct containing a promoter that is operable in a plant cell, operably linked to a coding sequence encoding a glutaredoxin protein of the present invention is used to transform a plant cell or cells. The transformed plant cell or cells are regenerated to produce transformed plants. These plants transformed with a construct comprising a functional promoter driving expression of a glutaredoxin protein-encoding polynucleotide of the invention demonstrated increased plant yield, i.e., increased above-ground biomass and/or and/or increased harvestable biomass and/or increased seed yield.

Now that it has been demonstrated that upregulation of glutaredoxin increases plant yield, other methods for increasing expression of an endogenous glutaredoxin sequence in a plant of interest can be used. The expression of a glutaredoxin gene present in a plant's genome can be altered by inserting a transcriptional enhancer upstream of the glutaredoxin gene present in the plant's genome. This strategy will allow the glutaredoxin gene's expression to retain its normal developmental profile, while showing elevated transcript levels. This strategy will occur through the insertion of an enhancer element upstream of a glutaredoxin gene of interest using a meganuclease designed against the genomic sequence of interest. Alternatively, a Cas9 endonuclease coupled with a guide RNA (gRNA) designed against the genomic sequence of interest, or a Cpf1 endonuclease coupled with a gRNA designed against the genomic sequence of interest, or a Csm1 endonuclease coupled with a gRNA designed against the genomic sequence of interest is used to effect the insertion of an enhancer element upstream of a glutaredoxin gene of interest. Alternatively, a deactivated endonuclease (e.g., a deactivated Cas9, Cpf1, or Csm1 endonuclease) fused to a transcriptional enhancer element is targeted to a genomic location near the transcription start site for a glutaredoxin gene of interest, thereby modulating the expression of said glutaredoxin gene of interest (Piatek et al. (2015) *Plant Biotechnol J* 13:578-589).

Modulation of the expression of a glutaredoxin protein-encoding gene may be achieved through the use of precise genome-editing technologies to modulate the expression of the endogenous sequence. In this manner, a nucleic acid sequence will be inserted proximal to a native plant sequence encoding the glutaredoxin through the use of methods available in the art. Such methods include, but are not limited to, meganucleases designed against the plant genomic sequence of interest (D'Halluin et al (2013) *Plant Biotechnol J* 11: 933-941); CRISPR-Cas9, CRISPR-Cpf1, TALENs, and other technologies for precise editing of genomes (Feng et al. (2013) *Cell Research* 23:1229-1232, Podevin et al. (2013) *Trends Biotechnology* 31: 375-383, Wei et al. (2013) *J Gen Genomics* 40: 281-289, Zhang et al (2013) WO 2013/026740, Zetsche et al. (2015) *Cell* 163: 759-771, U.S. Pat. No. 9,896,696, U.S. patent application Ser. No. 15/806,890); *N. gregoryi* Argonaute-mediated DNA insertion (Gao et al. (2016) *Nat Biotechnol* doi: 10.1038/nbt.3547); Cre-lox site-specific recombination (Dale et al. (1995) *Plant J* 7:649-659; Lyznik, et al. (2007) *Transgenic Plant J* 1:1-9; FLP-FRT recombination (Li et al. (2009) *Plant Physiol* 151:1087-1095); Bxb1-mediated integration (Yau et al. (2011) *Plant J* 701:147-166); zinc-finger mediated integration (Wright et al. (2005) *Plant J* 44:693-705); Cal et al. (2009) *Plant Mol Biol* 69:699-709); and homologous recombination (Lieberman-Lazarovich and Levy (2011) *Methods Mol Biol* 701: 51-65; Puchta (2002) *Plant Mol Biol* 48:173-182). The insertion of said nucleic acid sequences will be used to achieve the desired result of overexpression, decreased expression, and/or altered expression profile of a glutaredoxin gene.

Enhancers include any molecule capable of enhancing gene expression when inserted into the genome of a plant. Thus, an enhancer can be inserted in a region of the genome upstream or downstream of a glutaredoxin sequence of interest to enhance expression. Enhancers may be cis-acting, and can be located anywhere within the genome relative to a gene for which expression will be enhanced. For example, an enhancer may be positioned within about 1 Mbp, within about 100 kbp, within about 50 kbp, about 30 kbp, about 20 kbp, about 10 kbp, about 5 kbp, about 3 kbp, or about 1 kbp of a coding sequence for which it enhances expression. An enhancer may also be located within about 1500 bp of a gene for which it enhances expression, or may be directly proximal to or located within an intron of a gene for which it enhances expression. Enhancers for use in modulating the expression of an endogenous gene encoding a glutaredoxin protein or homolog according to the present invention include classical enhancer elements such as the CaMV 35S enhancer element, cytomegalovirus (CMV) early promoter enhancer element, and the SV40 enhancer element, and also intron-mediated enhancer elements that enhance gene expression such as the maize shrunken-1 enhancer element (Clancy and Hannah (2002) *Plant Physiol.* 130(2):918-29). Further examples of enhancers which may be introduced into a plant genome to modulate expression include a PetE enhancer (Chua et al. (2003) *Plant Cell* 15:11468-1479), or a rice α-amylase enhancer (Chen et al. (2002) *J. Biol. Chem.* 277:13641-13649), or any enhancer known in the art (Chudalayandi (2011) *Methods Mol. Biol.* 701:285-300). In some embodiments, the present invention comprises a subdomain, fragment, or duplicated enhancer element (Benfrey et al. (1990) *EMBO J* 9:1677-1684).

Alteration of glutaredoxin gene expression may also be achieved through the modification of DNA in a way that does not alter the sequence of the DNA. Such changes could include modifying the chromatin content or structure of the glutaredoxin gene of interest and/or of the DNA surrounding the glutaredoxin gene. It is well known that such changes in chromatin content or structure can affect gene transcription (Hirschhorn et al. (1992) *Genes and Dev* 6:2288-2298; Narlikar et al. (2002) *Cell* 108: 475-487). Such changes could also include altering the methylation status of the glutaredoxin gene of interest and/or of the DNA surrounding the glutaredoxin gene of interest. It is well known that such changes in DNA methylation can alter transcription (Hsieh (1994) *Mol Cell Biol* 14: 5487-5494). Targeted epigenome editing has been shown to affect the transcription of a gene in a predictable manner (Hilton et al. (2015) 33: 510-517). It will be obvious to those skilled in the art that other similar alterations (collectively termed "epigenetic alterations") to the DNA that regulates transcription of the glutaredoxin gene of interest may be applied in order to achieve the desired result of an altered glutaredoxin gene expression profile.

Alteration of glutaredoxin gene expression may also be achieved through the use of transposable element technologies to alter gene expression. It is well understood that transposable elements can alter the expression of nearby DNA (McGinnis et al. (1983) *Cell* 34:75-84). Alteration of the expression of a gene encoding a glutaredoxin may be achieved by inserting a transposable element upstream of the glutaredoxin gene of interest, causing the expression of said gene to be altered.

Alteration of glutaredoxin gene expression may also be achieved through expression of a transcription factor or transcription factors that regulate the expression of the glutaredoxin gene of interest. It is well understood that alteration of transcription factor expression can in turn alter the expression of the target gene(s) of said transcription factor (Hiratsu et al. (2003) *Plant J* 34:733-739). Alteration of glutaredoxin gene expression may be achieved by altering the expression of transcription factor(s) that are known to interact with a glutaredoxin gene of interest.

Alteration of glutaredoxin gene expression may also be achieved through the insertion of a promoter upstream of the open reading frame encoding a native glutaredoxin in the plant species of interest. This will occur through the insertion of a promoter of interest upstream of a glutaredoxin protein-encoding open reading frame using a meganuclease designed against the genomic sequence of interest. This strategy is well-understood and has been demonstrated previously to insert a transgene at a predefined location in the cotton genome (D'Halluin et al. (2013) *Plant Biotechnol J* 11: 933-941). It will be obvious to those skilled in the art that other technologies can be used to achieve a similar result of insertion of genetic elements at a predefined genomic locus by causing a double-strand break at said predefined genomic locus and providing an appropriate DNA template for insertion (e.g., CRISPR-Cas9, CRISPR-cpf1, CRISPR-Csm1, TALENs, and other technologies for precise editing of genomes).

The following examples are offered by way of illustration and not by way of limitation. All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

EXPERIMENTAL

Example 1—Construction of Glutaredoxin Plant Transformation Vectors

An open reading frame encoding a maize glutaredoxin protein was synthesized. This open reading frame comprised SEQ ID NO:1, encoding the protein sequence of SEQ ID NO:3. A second open reading from comprising SEQ ID NO:2, also encoding the protein sequence of SEQ ID NO:3, was also constructed with different codon usage from the codons in SEQ ID NO:1. Appropriate restriction sites were included at the 5' and 3' ends of the coding sequences to allow this DNA to be cloned into plant transformation vectors that contained genetic elements suitable for controlling gene expression. In each plant transformation construct, the glutaredoxin open reading frame was located downstream of a plant promoter and 5' untranslated region (5'UTR) and upstream of a 3'UTR. Table 2 summarizes the plant transformation constructs that were built containing a glutaredoxin open reading frame.

TABLE 2

Glutaredoxin plant transformation constructs

| Construct | Promoter + 5'UTR | ORF | 3'UTR |
|---|---|---|---|
| 130617 | 2X 35S (SEQ ID NO: 4) | GRMZM2G150295 (SEQ ID NO: 1, encoding SEQ ID NO: 3) | 35S poly A (SEQ ID NO: 5) |
| 131000 | ZmRbcS (SEQ ID NO: 6) | GRMZM2G150295 (SEQ ID NO: 1, encoding SEQ ID NO: 3) | ZmRbcS (SEQ ID NO: 7) |
| 131102 | 4xRGCGR (SEQ ID NO: 8) | GRMZM2G150295 (SEQ ID NO: 1, encoding SEQ ID NO: 3) | ZmCAl (SEQ ID NO: 9) |
| 131178 | GLDC (SEQ ID NO: 10) | GRMZM2G150295 (SEQ ID NO: 1, encoding SEQ ID NO: 3) | ZmRbcS (SEQ ID NO: 7) |
| 131186 | OsRbcS (SEQ ID NO: 11) | GRMZM2G150295 (SEQ ID NO: 1, encoding SEQ ID NO: 3) | OsRbcS (SEQ ID NO: 12) |
| 132450 | GLDC (SEQ. ID NO: 10) | GRMZM2G150295 (SEQ ID NO: 1, encoding SEQ ID NO: 3) | ZmRbcS (SEQ ID NO: 7) |
| 132451 | ZmRbcS (SEQ ID NO: 6) | GRMZM2G150295 (SEQ ID NO: 1, encoding SEQ ID NO: 3) | ZmRbcS (SEQ ID NO: 7) |
| 132460 | AtSBPase (SEQ ID NO: 13) | GRMZM2G150295 (SEQ ID NO: 2, encoding SEQ ID NO: 3) | AtSBPase (SEQ ID NO: 14) |

In addition to the gene cassettes described in Table 2, each plant transformation construct listed in Table 2 also contained a selectable marker cassette suitable for the selection of transformed plant cells and regeneration of plants following the introduction of the plant transformation vector, as described below. Each transformation vector was built in a plasmid that contained sequences suitable for plasmid maintenance in *E. coli* and in *Agrobacterium tumefaciens*. Following verification that the plant transformation constructs listed in Table 2 contained the desired sequences, they were transformed into *A. tumefaciens* cells for plant transformation. Alternatively, the constructs listed in Table 2 are used for plant transformation via biolistic particle bombardment.

Example 2—Transformation of *Setaria viridis*

*A. tumefaciens* cells harboring glutaredoxin plant transformation vectors were used to transform *S. viridis* cells according to a previously described method (PCT/US2015/43989, herein incorporated by reference). Following transformation of the *S. viridis* cells with the relevant plant transformation vectors and regeneration of *S. viridis* plants, PCR analyses were performed to confirm the presence of the gene(s) of interest in the *S. viridis* genome. Table 3 summarizes the transformation constructs used to transform *S.* viridis, along with the number of PCR-verified transgenic plants that resulted from transformation with each construct.

TABLE 3

Summary of *S. viridis* transformation with glutaredoxin plant transformation vectors

| Construct | # Events |
| --- | --- |
| 130617 | 45 |
| 131000 | 19 |
| 131102 | 9 |
| 131178 | 32 |

Example 3—Transformation of Maize (*Zea mays*)

*A. tumefaciens* cells harboring the 132450 vector were used to transform maize (*Zea mays* cv. B104) cells suitable for regeneration on tissue culture medium. Additional glutaredoxin plant transformation vectors are used to transform maize (*Zea mays* cv. B104) cells suitable for regeneration on tissue culture medium using *A. tumefaciens* or biolistic particle bombardment methods. Following transformation of the maize cells with the relevant plant transformation vectors and regeneration of maize plants, PCR analyses are performed to confirm the presence of the gene(s) of interest in the maize genome.

Example 4—Transformation of Rice (*Oryza sativa*)

*A. tumefaciens* cells harboring glutaredoxin plant transformation vectors are used to transform rice (*Oryza sativa* cv. Kitaake) cells suitable for regeneration on tissue culture medium. Following transformation of the rice cells with the relevant plant transformation vectors and regeneration of rice plants, PCR analyses are performed to confirm the presence of the gene(s) of interest in the rice genome.

Example 5—Characterization of Transgenic *S. viridis*

Following the transformation and regeneration of *S. viridis* plants transformed with a glutaredoxin plant transformation vector, the T0-generation plants were cultivated to maturity to produce T1-generation seeds. T1-generation *S. viridis* plants harboring the glutaredoxin gene cassette of interest were grown in a greenhouse setting to assess the effects of glutaredoxin gene expression on plant growth and terminal above-ground biomass and seed yield. A randomized block design was used with a wild-type *S. viridis* border row to eliminate edge effects from the analysis. Null segregant plants were grown alongside the transgenic *S. viridis* plants in identical environmental conditions. Table 4 summarizes the results of the biomass and seed yield determinations made from experiments with T1-generation *S. viridis* plants harboring a glutaredoxin gene cassette as a result of transformation. This table indicates the construct used for transformation, as described in Table 2, followed by the T0 event number from which the T1 seed was harvested.

TABLE 4

Summary of *S. viridis* greenhouse observations with T1-generation plants

| | DW (g) | Seed Yield (g) | DW Change | Seed Change |
| --- | --- | --- | --- | --- |
| 130617.10b | 2.12 ± 0.13 | 0.16 ± 0.01 | −24.1% | −46.9% |
| 130617.19a | 2.46 ± 0.21 | 0.29 ± 0.03 | −11.6% | −6.0% |
| 130617.20a | 2.12 ± 0.35 | 0.19 ± 0.03 | −24.0% | −38.2% |
| 130617.7a | 1.81 ± 0.14 | 0.27 ± 0.04 | −35.0% | −13.2% |
| WT | 2.79 ± 0.28 | 0.31 ± 0.04 | n/a | n/a |
| 131102-1 | 2.83 ± 0.37 | 0.48 ± 0.08 | −26.0% | −27.7% |
| 131102-2 | 3.54 ± 0.45 | 0.57 ± 0.12 | −7.3% | −13.3% |
| 131102-3A | 2.86 ± 0.54 | 0.44 ± 0.11 | −25.1% | −32.9% |
| 131102-5B | 2.99 ± 0.44 | 0.50 ± 0.09 | −21.9% | −23.9% |
| 131102-Null | 3.82 ± 0.45 | 0.66 ± 0.12 | n/a | n/a |
| 131178-10 | 2.90 ± 0.19 | 0.73 ± 0.07 | −0.5% | 10.2% |
| 131178-11 | 3.28 ± 0.13 | 0.95 ± 0.03 | 12.4% | 42.3% |
| 131178-20 | 3.11 ± 0.20 | 0.93 ± 0.11 | 6.6% | 39.1% |
| 131178-29 | 2.23 ± 0.30 | 0.59 ± 0.10 | −23.5% | −11.0% |
| 131178-6 | 3.23 ± 0.34 | 0.80 ± 0.05 | 10.8% | 20.5% |
| 131178-7 | 2.88 ± 0.18 | 0.80 ± 0.07 | −1.3% | 20.2% |
| 131178-Null | 2.92 ± 0.11 | 0.67 ± 0.05 | n/a | n/a |

In Table 4, the dry weight of the above-ground biomass is indicated in the DW column in grams. Similarly, the dry weight of the harvested seeds is indicated in grams in the Seed Yield column. The DW Change and Seed Change columns indicate the percent change in above-ground biomass and seed yield, respectively, relative to the null segregants from the appropriate construct. Because an insufficient number of null segregant controls from the 130617 construct were available, wild-type *S. viridis* controls were used to assess changes in biomass accumulation and seed yield for events from this construct. As this table shows, constructs 130617 and 131102 resulted in decreased biomass and seed yield relative to null or wild-type controls. The 131178 construct, however, resulted in biomass increases in three of the six events tested and seed yield increases in five of the six events tested relative to null segregant controls.

T2 events resulting from self-pollination of the 131178 T1 events listed in Table 4 were tested in a biomass assay using the same methods described above. Table 5 summarizes the results of these T2 generation biomass and seed yield assays.

TABLE 5

Summary of *S. viridis* greenhouse observations with T2-generation plants

| | DW (g) | Seed Yield (g) | DW Change | Seed Change |
| --- | --- | --- | --- | --- |
| 131178-10 | 4.55 ± 0.21 | 1.13 ± 0.08 | −10.4% | 11.6% |
| 131178-11 | 4.93 ± 0.12 | 1.22 ± 0.07 | −3.0% | −34.8% |
| 131178-20 | 5.34 ± 0.23 | 1.10 ± 0.07 | 5.1% | 24.6% |
| 131178-29 | 4.82 ± 0.15 | 1.03 ± 0.08 | −5.1% | −20.3% |
| 131178-6 | 4.79 ± 0.17 | 1.00 ± 0.11 | −5.7% | −11.6% |
| 131178-7 | 5.04 ± 0.21 | 1.06 ± 0.09 | −0.8% | 11.6% |
| 131178-null | 5.08 ± 0.15 | 1.07 ± 0.06 | n/a | n/a |

Example 6—Characterization of Transgenic Maize

T0-generation maize plants transformed with the glutaredoxin plant transformation vector of interest and confirmed to contain the gene(s) of interest are grown to maturity in a greenhouse. When the T0 plants reach reproductive stages, they are pollinated by an appropriate inbred maize line to produce hybrid maize seeds. Alternatively, or in addition to pollination of the T0 transgenic maize plant, the pollen from the T0 is used to pollinate one or more inbred maize lines to produce hybrid maize seeds. The F1-generation hybrid seed resulting from these pollinations are planted in a field setting in two- or four-row plots and cultivated using standard agronomic practices. Plants are genotyped to determine which plants do and which do not contain the glutaredoxin gene cassette and any other relevant gene cassettes (e.g., a selectable marker gene cassette) that were included in the glutaredoxin plant transformation vector. Following the maturation of the maize plants, the seed is harvested. Seeds from the plants containing the glutaredoxin gene cassette are pooled, as are seeds from the null segregant plants lacking the glutaredoxin gene cassette. The seeds are weighed, and seed yields are calculated for the plants containing the glutaredoxin gene cassette as well as for the null segregant plants lacking the glutaredoxin gene cassette. Appropriate statistical analyses are performed to determine whether plants containing a glutaredoxin reductase gene cassette produce higher yields than those plants that lack a glutaredoxin gene cassette.

Alternatively, T0-generation maize plants transformed with the glutaredoxin plant transformation vector of interest and confirmed to contain the gene(s) of interest are grown to maturity in a greenhouse, then self-pollinated. The resulting T1 seeds are planted in a greenhouse and the T1 plants are cultivated. T1 plants are genotyped to identify homozygous, heterozygous, and null segregant plants. Pollen from homozygous T1 plants is used to pollinate one or more inbred maize lines to produce hybrid maize seeds. Pollen from null segregant plants is also used to pollinate one or more inbred maize lines to produce hybrid maize seeds. The resulting hybrid seeds are planted in a field setting in two- or four-row plots and cultivated using standard agronomic practices. Following the maturation of the maize plants, the seed is harvested. Seeds from the plants containing the glutaredoxin gene cassette are pooled, as are seeds from the null segregant plants lacking the glutaredoxin gene cassette. The seeds are weighed, and seed yields are calculated for the plants containing the glutaredoxin gene cassette as well as for the null segregant plants lacking the glutaredoxin gene cassette. Appropriate statistical analyses are performed to determine whether plants containing a glutaredoxin gene cassette produce higher yields than those plants that lack a glutaredoxin gene cassette.

Example 7—Characterization of Transgenic Rice

T0-generation rice plants transformed with the glutaredoxin plant transformation vector of interest and confirmed to contain the gene(s) of interest are grown to maturity in a greenhouse, then self-pollinated. The resulting T1 seeds are planted in a greenhouse and the T1 plants are cultivated. T1 plants are genotyped to identify homozygous, heterozygous, and null segregant plants. The plants from each group are grown to maturity and allowed to self-pollinate to produce T2 seed. The T2 seed resulting from this self-pollination is harvested and weighed, and seed yields from homozygous, heterozygous, and null segregant plants are calculated. Appropriate statistical analyses are performed to determine whether plants containing a glutaredoxin gene cassette produce higher yields than those plants that lack a glutaredoxin gene cassette.

T1-generation plants grown from seed that resulted from self-pollination of T0-generation plants, or T2-generation plants grown from seed that resulted from self-pollination of homozygous T1-generation plants, are grown in a field setting. In the case of T2-generation plants, null-segregant T1-generation plants are also self-pollinated to produce T2-generation null plants as negative controls. The plants are cultivated using standard agronomic practices and allowed to reach maturity. Upon reaching maturity, the plants are allowed to self-pollinate. The seed resulting from these self-pollinations is harvested and weighed, and seed yields from homozygous, heterozygous, and null segregant plants are calculated. Appropriate statistical analyses are performed to determine whether plants containing a glutaredoxin gene cassette produce higher yields than those plants that lack a glutaredoxin gene cassette.

I claim:

1. A method for increasing crop yield comprising transforming a plant with at least one glutaredoxin protein-encoding sequence;
    wherein the glutaredoxin protein-encoding sequence encodes a protein which shares at least 80% sequence identity with SEQ ID NO 3;
    wherein the glutaredoxin protein-encoding sequence is operably linked to a heterologous bundle sheath cell-preferred promoter which comprises SEQ ID NO 10.

2. The method of claim 1, wherein said glutaredoxin protein-encoding sequence comprises a sequence selected from the group of SEQ ID NOs:1 and 2, or encodes a protein selected from the group consisting of SEQ ID NOs:3-, 15-17, 18, 20, 21, 24-26 and 29.

3. A plant having stably incorporated into its genome a promoter that drives expression in a plant operably linked to a glutaredoxin protein-encoding sequence, wherein said promoter is heterologous to said glutaredoxin protein-encoding sequence;
    wherein the glutaredoxin protein-encoding sequence encodes a protein which shares at least 80% sequence identity with SEQ ID NO: 3;
    wherein the heterologous bundle sheath cell-preferred promoter comprises SEQ ID NO: 10.

4. The plant of claim 3, wherein said glutaredoxin protein-encoding sequence comprises a sequence selected from the group of SEQ ID NOs:1 and 2, or encodes a protein selected from the group consisting of SEQ ID NOs:3-, 15-17, 18, 20, 21, 24-26 and 29.

5. Transformed seed of the plant of claim 3, wherein said transformed seed comprises the said glutaredoxin protein-encoding sequence operably linked to the said promoter that is heterologous to said glutaredoxin protein-encoding sequence.

6. The plant of claim 3 wherein said plant is a monocot.

7. The plant of claim 3 wherein said plant is a dicot.

8. The method of claim 1, wherein said glutaredoxin protein-encoding sequence is expressed from a bundle sheath cell-preferred promoter.

9. The plant of claim 3, wherein said promoter that drives expression in a plant is a bundle sheath cell-preferred promoter.

10. A DNA construct comprising, in operable linkage,
    a. A promoter that is functional in a plant cell, wherein the said promoter is a bundle sheath cell-preferred promoter which comprises SEQ ID NO: 10; and,
    b. A nucleic acid sequence encoding a glutaredoxin protein which shares at least 80% sequence identity with SEQ ID NO: 3.

11. The DNA construct of claim 10, wherein said nucleic acid sequence encoding a glutaredoxin protein comprises a sequence selected from the group of SEQ ID NOs:1 and 2, or encodes a protein selected from the group consisting of SEQ ID NOs:3, 15-17, 18, 20, 21, 24-26 and 29.

12. The DNA construct of claim 10, wherein said promoter is heterologous to said nucleic acid sequence encoding a glutaredoxin protein.

* * * * *